United States Patent
Urbanski et al.

(10) Patent No.: US 6,489,321 B1
(45) Date of Patent: Dec. 3, 2002

(54) NONPEPTIDE SUBSTITUTED BENZOTHIAZEPINES AS VASOPRESSIN ANTAGONISTS

(75) Inventors: Maud J. Urbanski, Belle Mead, NJ (US); Robert H. K. Chen, Belle Mead, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/704,314

(22) Filed: Nov. 2, 2000

Related U.S. Application Data

(60) Provisional application No. 60/163,544, filed on Nov. 4, 1999.

(51) Int. Cl.[7] ............... C07D 281/10; A61K 31/554; A61P 9/10
(52) U.S. Cl. ............... 514/211.05; 514/211.09; 540/523; 540/552
(58) Field of Search ............... 540/523, 552; 514/211.05, 211.09

(56) References Cited

U.S. PATENT DOCUMENTS

| | | | |
|---|---|---|---|
| 5,300,513 A | 4/1994 | Ogawa et al. | 514/312 |
| 5,681,841 A | 10/1997 | Himmelsbach et al. | 514/326 |
| 5,656,642 A | 12/1997 | Fujioka et al. | 514/326 |
| 5,880,284 A | 3/1999 | Himmelsbach et al. | 546/133 |
| 5,952,322 A | 9/1999 | Hoover et al. | 514/210 |
| 6,057,338 A | 5/2000 | Yang et al. | 514/321 |
| 6,268,360 B1 | 7/2001 | Failli et al. | 514/220 |

FOREIGN PATENT DOCUMENTS

| | | |
|---|---|---|
| EP | 0587134 A3 | 3/1994 |
| EP | 0587134 A2 | 3/1994 |
| JP | 2-184681 * | 7/1990 |
| JP | 05320135 A | 12/1993 |
| JP | 06080641 A | 3/1994 |
| WO | WO 91/05549 A1 | 5/1991 |
| WO | WO 96/39384 A1 | 12/1996 |
| WO | WO 96/39385 A1 | 12/1996 |
| WO | WO 97/30707 A1 | 8/1997 |
| WO | WO 98/11128 A1 | 3/1998 |
| WO | WO 98/44922 A1 | 10/1998 |
| WO | WO 98/45285 A1 | 10/1998 |
| WO | WO 99/24051 A2 | 5/1999 |
| WO | WO 99/24051 A3 | 5/1999 |
| WO | 99/37637 A1 | 7/1999 |
| WO | WO 99/64401 A2 | 12/1999 |
| WO | WO 00/18764 A1 | 4/2000 |
| WO | WO 00/26203 A1 | 5/2000 |

* cited by examiner

Primary Examiner—Bruck Kifle

(57) ABSTRACT

The invention is directed to nonpeptide substituted benzodiazepines of Formula I,

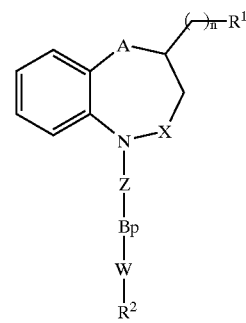

wherein A, X, Z, Bp, W, n, $R^1$ and $R^2$ are as described in the specification, which are useful as vasopressin receptor antagonists for treating conditions involving increased vascular resistance and cardiac insufficiency. Pharmaceutical compositions comprising a compound of Formula I and methods of treating conditions such as hypertension, congestive heart failure, cardiac insufficiency, coronary vasospasm, cardiac ischemia, liver cirrhosis, renal vasospasm, renal failure, cerebral edema and ischemia, stroke, thrombosis, or water retention are also disclosed.

27 Claims, No Drawings

NONPEPTIDE SUBSTITUTED BENZOTHIAZEPINES AS VASOPRESSIN ANTAGONISTS

CROSS REFERENCE TO RELATED APPLICATIONS

This application claims priority from U.S. Ser. No. 60/163,544, filed Nov. 4, 1999.

FIELD OF THE INVENTION

This invention relates to novel nonpeptide substituted vasopressin receptor antagonists. More particularly, the compounds of the present invention interrupt the binding of the peptide hormone vasopressin to its receptors and are therefore useful for treating conditions involving increased vascular resistance and cardiac insufficiency.

BACKGROUND OF THE INVENTION

Vasopressin is a nonpeptide hormone that is secreted primarily from the posterior pituitary gland. The hormone effects its actions through the vascular V-1 and renal V-2 receptor subtypes. The functions of vasopressin include contraction of uterine, bladder, and smooth muscle; stimulation of glycogen breakdown in the liver; release of corticotropin from the anterior pituitary; induction of platelet aggregation; and central nervous system modulation of behaviors and stress responses. The V-1 receptor mediates the contraction of smooth muscle, and hepatic glycogenolytic and central nervous system effects of vasopressin. The V-2 receptor, presumably found only in the kidney, effects the antidiuretic actions of vasopressin via stimulation of adenylate cyclase.

Elevated plasma vasopressin levels appear to play a role in the pathogenesis of congestive heart failure (P. A. Van Zwieten, Progr. *Pharmacol. Clin. Pharmacol.* 1990, 7, 49). As progress toward the treatment of congestive heart failure, nonpeptide vasopressin V-2 receptor antagonists have induced low osmolality aquaresis and decreased peripheral resistance in conscious dogs with congestive heart failure (H. Ogawa, *J. Med. Chem.* 1996, 39, 3547). In certain pathological states, plasma vasopressin levels may be inappropriately elevated for a given osmolality, thereby resulting in renal water retention and hyponatremia. Hyponatremia, associated with edematous conditions (cirrhosis, congestive heart failure, renal failure), can be accompanied by the syndrome of inappropriate secretion of antidiuretic hormone (SIADH). Treatment of SIADH-compromised rats with a vasopressin V-2 antagonist has corrected their existing hyponatremia (G. Fujisawa, *Kidney Int.* 1993, 44(1), 19). Due in part to the contractile actions of vasopressin at its V-1 receptor in the vasculature, vasopressin V-1 antagonists have reduced blood pressure as a potential treatment for hypertension as well. Thus, vasopressin receptor antagonists could be useful as therapeutics in the conditions of hypertension, congestive heart failure/cardiac insufficiency, coronary vasospasm, cardiac ischemia, liver cirrhosis, renal vasospasm, renal failure, cerebral edema and ischemia, stroke, thrombosis, and water retention.

SUMMARY OF THE INVENTION

The present invention is directed to compounds represented by the following formula I:

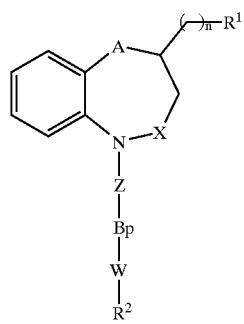

wherein
  $R^1$ is selected from —COOH, formyl, o-mesylate, —SO$_2$OH, alkoxysulfonyl, alkylcarboxy, substituted alkylcarboxy, aralcarboxy, substituted aralcarboxy, —NR$^4$R$^5$, —OH, cyano, N-morpholino, alkoxy, aralkoxy, alkylcarbamoyl, substituted alkylcarbamoyl, alkoxycarbonyl, substituted alkoxycarbonyl, —NHCOR$^6$ and —CONR $^7$R$^8$, wherein
    $R^4$, $R^5$, $R^6$, and $R^8$ are independently selected from the group consisting of H, alkyl, and aryl;
  A is S, SO or SO$_2$;
  X is CH$_2$ or carbonyl;
  Z is CH$_2$, SO$_2$ or carbonyl, with the proviso that X is not CH$_2$ when Z is CH$_2$;
  B is (CH$_2$)$_m$, NH or O;
  W is aryl, substituted aryl, heteroaryl or substituted heteroaryl;
  $R^2$ is —N(H)YR$^3$ or —YN(H)R$^3$ wherein Y is H or carbonyl;
  $R^3$ is H, alkyl, substituted alkyl, aryl or substituted aryl;
  m is 1–3;
  n is 1–5; and
  p is 0 or 1.

The compounds of the present invention are vasopressin receptor antagonists useful as aquaretics and, in general, in disease states of vascular resistance.

Illustrative of the invention is a pharmaceutical composition comprising a pharmaceutically acceptable carrier and any of the compounds described above. Illustrating the invention is a pharmaceutical composition made by mixing any of the compounds described above and a pharmaceutically acceptable carrier. An illustration of the invention is a process for making a pharmaceutical composition comprising mixing any of the compounds described above and a pharmaceutically acceptable carrier.

An example of the invention is a method of treating congestive heart failure in a subject in need thereof comprising administering to the subject a therapeutically effective amount of any of the compounds or pharmaceutical compositions described above.

Another example of the invention is a method of inhibiting the onset of a condition of vascular resistance in the subject, which comprises administering to the subject a prophylactically effective dose of the pharmaceutical composition of a compound of Formula I.

Further exemplifying the invention is the method of treating congestive heart failure, wherein the therapeutically effective amount of the compound is about 1 to about 30 mg/kg/day.

Still further exemplifying the invention is the method of inhibiting the onset of congestive heart failure, wherein the prophylactically effective amount of the compound is about 1 to about 30 mg/kg/day.

An additional illustration of the invention is a method of treating a condition selected from hypertension, congestive heart failure, cardiac insufficiency, coronary vasospasm, cardiac ischemia, liver cirrhosis, renal vasospasm, renal failure, cerebral edema and ischemia, stroke, thrombosis, or water retention in a subject in need thereof comprising administering to the subject a therapeutically effective amount of any of the compounds or pharmaceutical compositions described above. Preferably, the therapeutically effective amount of the compound administered for treating any of these conditions is about 1 to about 30 mg/kg/day.

Also included in the invention is the use of any of the compounds described above for the preparation of a medicament for treating a condition selected from inner ear disorders, hypertension, congestive heart failure, cardiac insufficiency, coronary vasospasm, cardiac ischemia, liver cirrhosis, renal vasospasm, renal failure, cerebral edema and ischemia, stroke, thrombosis, or water retention in a subject in need thereof.

DETAILED DESCRIPTION OF THE INVENTION

The present invention provides nonpeptide substituted benzothiazepine compounds which are useful as antagonists of vasopressin. More particularly, the compounds of Formula I inhibit the binding of vasopressin to V-1 and V-2 receptors, and are therefore useful in treating conditions with increased vascular resistance. Examples of conditions with increased vascular resistance include, but are not limited to, congestive heart failure, edema, water retaining states, and the like. More particularly, the present invention is directed to compounds of Formula I:

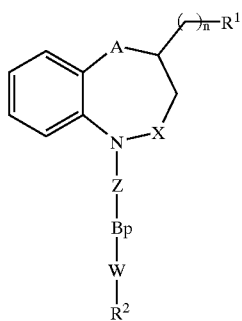

I wherein
$R^1$ is selected from —COOH, formyl, o-mesylate, —SO$_2$OH, alkoxysulfonyl, alkylcarboxy, substituted alkylcarboxy, aralcarboxy, substituted aralcarboxy, —NR$^4$R$^5$, —OH, cyano, N-morpholino, alkoxy, aralkoxy, alkylcarbamoyl, substituted alkylcarbamoyl, alkoxycarbonyl, substituted alkoxycarbonyl, —NHCOR$^6$ and —CONR$^7$R$^8$, wherein
$R^4$, $R^5$, $R^6$, $R^7$, and $R^8$ are independently selected from the group consisting of H, alkyl, and aryl;
A is S, SO or SO$_2$;
X is CH$_2$ or carbonyl;
Z is CH$_2$, SO$_2$ or carbonyl, with the proviso that X is not CH$_2$ when Z is CH$_2$;
B is (CH$_2$)$_m$, NH or O;
W is aryl, substituted aryl, heteroaryl or substituted heteroaryl;

$R^2$ is —N(H)YR$^3$ or —YN(H)R$^3$ wherein Y is H or carbonyl;
$R^3$ is H, alkyl, substituted alkyl, aryl or substituted aryl;
m is 1–3;
n is 1–5; and
p is 0 or 1.

The nonpeptide substituted benzodiazepine compounds of the present invention are vasopressin receptor antagonists, in a preferred embodiment, the compounds are orally active. As demonstrated by the results of the pharmacological studies described hereinafter, the compounds show the ability to block vasopressin binding to recombinant V-1 and V-2, and therefore are useful as therapeutics in or prophylactics against the conditions of hypertension, congestive heart failure/cardiac insufficiency, coronary vasospasm, cardiac ischemia, liver cirrhosis, renal vasospasm, renal failure, cerebral edema and ischemia, stroke, thrombosis, and water retention.

In particular, compounds of Formula I, wherein $R^1$ is —COOH, formyl, o-mesylate, —SO$_2$OH, alkylcarboxy, substituted alkylcarboxy, aralcarboxy, substituted aralcarboxy, cyano, N-morpholino, alkoxy, aralkoxy, alkylcarbamoyl, or substituted alkylcarbamoyl, are embodiments of the present invention.

More particularly, compounds of Formula I wherein A is S, p is 0, and n is 1 or 2 are embodiments of this invention.

Compounds of Formula I wherein X is CH$_2$ and Z is carbonyl, are also particular embodiments of this invention.

Compounds of Formula I wherein W is phenyl, substituted phenyl, benzyl, substituted benzyl, pyridinyl, substituted pyridinyl, naphthyl or substituted naphthyl, are still particular embodiments of this invention.

Compounds of Formula I, wherein $R^2$ is —N(H)YR$^3$ in which Y is carbonyl and $R^3$ is substituted phenyl, are further particular embodiments of the present invention. In particular, compounds of Formula I wherein $R^2$ is —NHCO (2-Ph)Ph are yet other embodiments of the present invention.

Compounds of Formula I, wherein $R^3$ is phenyl or substituted phenyl, are still other embodiments of the present invention.

In addition, compounds of Formula I, wherein $R^1$ is amine, substituted amine, —NHCOR$^6$ or —CONR$^7$R8 wherein $R^6_1$, $R^7$ and $R^8$ are as described hereinabove, are particular embodiments of the present invention.

More particularly, compounds of Formula I wherein
$R^1$ is selected from —NH$_2$, —NHCH$_3$, —N(CH$_3$)$_2$, —NHBOC, —N(BOC;)$_2$, —NHCOC (CH$_3$)$_2$NH$_2$, —N(COC (CH$_3$)$_2$NH$_2$)$_2$ and —NCH$_2$ (2,5—OCH$_3$)Ph;
W is Ph or substituted Ph;
$R^2$ is —NH$_2$, —NHAc, —NHCO(2-CH$_3$)Ph or —NHCO (2-Ph)Ph; and
p is 0
are also particular embodiments of the present invention.

Compounds of Formula I wherein $R^1$ is —OH are particular embodiments of the present invention, too.

More particularly, compounds of Formula I wherein
$R^1$ is —OH;
W is heteroaryl, Ph or substituted Ph;
$R^2$ is —NH$_2$, —NHAc, —NHCOCH$_3$, —NHCO(2-CH$_3$)Ph, —NHCO(2-Ph)Ph, —NHCO(2-CH$_3$,5-F)Ph, or —NHCO(3,4-Cl)Ph; and
p is 0
are also particular embodiments of the present invention.

Compounds of Formula I wherein $R^1$ is alkoxycarbonyl, substituted alkoxycarbonyl, or —$CONR^7R^8$ wherein $R^7$ and $R^8$ are as described hereinabove, are particular embodiments of the present invention as well.

More particularly, compounds of Formula I wherein $R^1$ is alkoxycarbonyl, substituted alkoxycarbonyl, or —$CONR^7R^8$ wherein $R^7$ and $R^8$ are as described hereinabove;

Z is carbonyl;

W is Ph or substituted Ph;

$R^2$ is —NHCO(2-Ph)Ph; and p is 0 are also particular embodiments of the present invention.

The following compounds are further particular embodiments of the present invention:

Compound 24: 2-Carboxymethyl-1-oxo-5-(4-(2-phenylbenzoylamino)benzoyl)-1,5-benzothiazepine

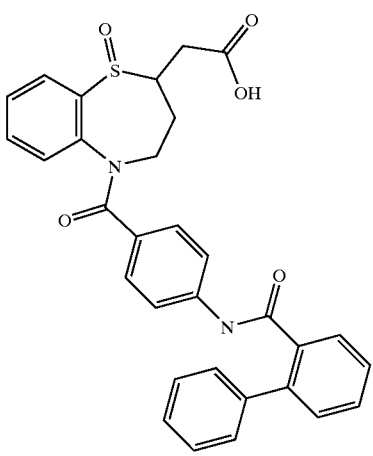

Compound 29: 2-Carboxymethyl-5-(4-(2-phenylbenzolylamino)benzoyl)-1,5-benzothiazepine

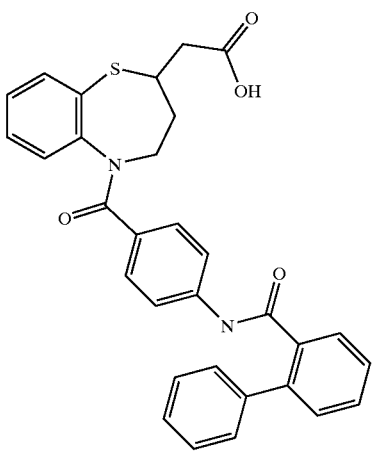

Compound 31: 2-(2-Carboxyethyl)-5-[4-(2-phenylbenzoylamino)benzoyl]-1,5-benzothiazepine

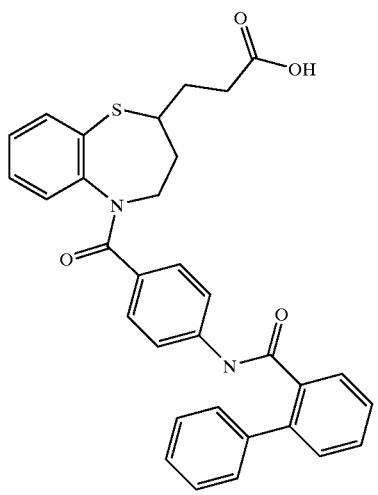

Compound 33 and Compound 34: 2-Carboxymethyl-5-[4-(2-phenylbenzoylamino)benzoyl]-1, 5-benzothiazepine

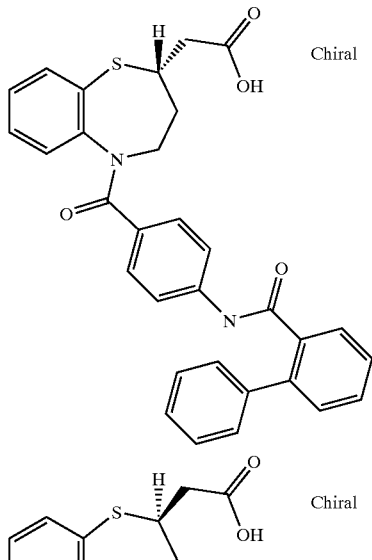

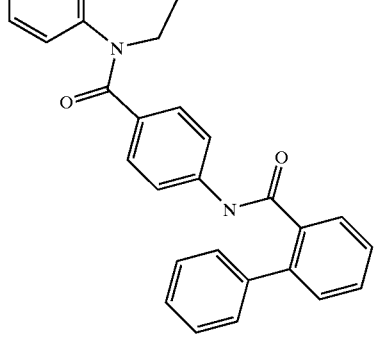

The compounds of the present invention may also be present in the form of a pharmaceutically acceptable salt or salts. For use in medicine, the salt or salts of the compounds of this invention refer to non-toxic "pharmaceutically acceptable salt or salts." Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid. Representative basic/cationic salts include, but are not limited to, benzathine, chloroprocaine, choline, diethanolamine, ethylenediamine, meglumine, procaine, aluminum, calcium, lithium, magnesium, potassium, sodium, or zinc.

Where the compounds according to this invention have at least one stereogenic center, they may accordingly exist as enantiomers. Where the compounds possess two or more stereogenic centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The term "subject" as used herein, refers to an animal, preferably a mammal, most preferably a human, who has been the object of treatment, observation or experiment.

As used herein, "treating" a disorder means eliminating or otherwise ameliorating the cause and/or effects thereof. To "inhibit" or "inhibiting" the onset of a disorder means preventing, delaying or reducing the likelihood of such onset.

Methods are known in the art for determining therapeutically and prophylactically effective doses for the instant pharmaceutical composition. The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. The term "prophylactically effective amount" refers to that amount of active compound or pharmaceutical agent that inhibits in a subject the onset of a disorder as being sought by a researcher, veterinarian, medical doctor or other clinician, the delaying of which disorder is mediated by the reduction of increased vascular resistance.

Unless otherwise noted, under standard nomenclature used throughout this disclosure the terminal portion of the designated side chain is described first, followed by the adjacent functionality toward the point of attachment.

Unless otherwise noted, "alkyl" and "alkoxy" as used herein, whether used alone or as part of a substituent group, include straight and branched chains having 1 to 8 carbon atoms, or any number within this range. For example, alkyl radicals include methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are oxygen ethers formed from the previously described straight or branched chain alkyl groups. Cycloalkyl groups contain 3 to 8 ring carbons and preferably 5 to 7 rung carbons.

The term "Ar" or "aryl" as used herein, whether used alone or as part of a substituent group, refers to an aromatic group such as phenyl and naphthyl. When the Ar or aryl group is substituted, it may have one to three substituents which are independently selected from $C_1$–$C_8$ alkyl, $C_1$–$C_8$ alkoxy, fluorinated $C_1$–$C_8$ alkyl (e.g., trifluoromethyl), fluorinated $C_1$–$C_8$ alkoxy (e.g., trifluoromethoxy), halogen, cyano, hydroxy, amino, nitro, $C_1$–$C_4$ alkylamino (i.e., —NH—$C_1$–$C_4$ alkyl), $C_1$–$C_4$ dialkylamino (i.e., —N—[$C_1$–$C_4$ alkyl]$_2$ wherein the alkyl groups can be the same or different), or unsubstituted, mono-, di- or tri-substituted phenyl wherein the substituents on the phenyl are independently selected from $C_1$–$C_8$ alkyl, $C_1$–$C_8$ alkoxy, fluorinated $C_1$–$C_8$ alkyl, fluorinated $C_1$–$C_8$ alkoxy, halogen, cyano, hydroxy, amino, nitro, alkylamino, dialkylamino or heteroaryl. "Ph" or "PH" denotes phenyl.

The term "heteroaryl" as used herein represents a stable five or six membered monocyclic aromatic ring system which consists of carbon atoms and from one to three heteroatoms selected from N, O or S. The heteroaryl group may be attached at any heteroatom or carbon atom which results in the creation of a stable structure. Examples of heteroaryl groups include, but are not limited to pyridinyl, pyrazinyl, pyridazinyl, pyrimidinyl, thiophenyl, furanyl, imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, benzopyrazolyl, indolyl, benzothiazolyl, benzothiadiazolyl, benzotriazolyl or quinolinyl. Prefered heteroaryl groups include pyridinyl, thiophenyl, furanyl and quinolinyl. When the heteroaryl group is substituted, the heteroaryl group may have one to three substituents which are independently selected from $C_1$–$C_8$ alkyl, halogen, aryl, heteroaryl, alkoxy, alkylamino, dialkylamino, arylamino, nitro, and hydroxy.

The term "aralkoxy" indicates an alkoxy group substituted with an aryl group (e.g., benzyloxy).

The term "acyl" as used herein, whether used alone or as part of a substituent group, means an organic radical having 2 to 6 carbon atoms (branched or straight chain) derived from an organic acid by removal of the hydroxyl group.

The term "halogen" shall include iodine, bromine, chlorine and fluorine.

The terms "substituted alkylcarboxy," "substituted aralcarboxy" and "substituted alkylcarbamoyl" denote alkylcarboxy, aralcarboxy and alkylcarbamoyl substituted with radicals including, but not limited to, halogen, alkyl, alkoxy, amino, and the like.

Whenever the term "alkyl", "acyl", or "aryl" or either of their prefix roots appear in a name of a substituent (e.g., aralkyl, dialkylamino) it shall be interpreted as including those limitations given above for "alkyl", "acyl", and "aryl." Designated numbers of carbon atoms (e.g., $C_1$–$C_6$) shall refer independently to the number of carbon atoms in an alkyl or cycloalkyl moiety or to the alkyl portion of a larger substituent in which alkyl appears as its prefix root.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

As used herein, the term "composition" is intended to encompass a product comprising the specified ingredients in the specified amounts, as well as any product which results, directly or indirectly, from combinations of the specified ingredients in the specified amounts.

The utility of the compounds to treat disorders of increased vascular resistance can be determined according to the procedures described herein. The present invention therefore provides a method of treating vascular resistance disorders in a subject in need thereof which comprises administering any of the compounds as defined herein in a quantity effective to treat vascular resistance disorders. The compound may be administered to a patient by any conventional route of administration, including, but not limited to, intravenous, oral, subcutaneous, intramuscular, intradermal and parenteral.

The present invention also provides pharmaceutical compositions comprising one or more compounds of this invention in association with a pharmaceutically acceptable carrier.

To prepare the pharmaceutical compositions of this invention, one or more compounds of Formula I or salt thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 1 mg to 30 mg/kg and may be given at a dosage of from about 1 to 30 mg/kg/day (preferred 3 to 15 mg/kg/day). The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation. The compounds may also be resolved by formation of diastereomeric esters or amides, followed by chromatographic separation and removal of the chiral auxiliary. Alternatively, the compounds may be resolved using a stereogenic HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

This invention will be better understood by reference to the schemes and examples that follow, but those skilled in the art will readily appreciate that these are only illustrative of the invention as described more fully in the claims which follow thereafter.

Scheme 1

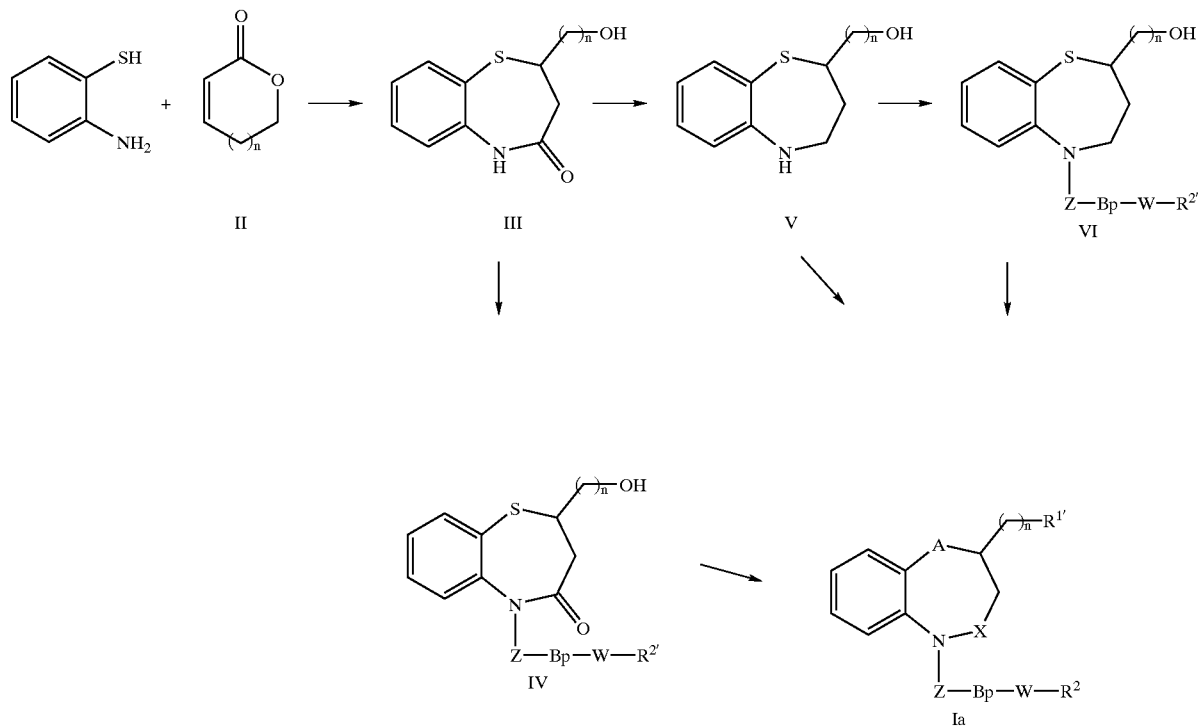

As set forth in Scheme 1, wherein $R^{1'}$ is —COOH, formyl, alkoxy, aralkoxy, or —O(CO)$R^9$, $R^9$ is alkyl, substituted alkyl, aryl or substituted aryl, $R^2$ is nitro, —N(H)Y$R^3$ or —YN(H)$R^3$, and A, X, Z, Bp, W, Y, $R^2_1$, $R^3_1$, n are as described above, a base such as triethylamine is added to a mixture of 2-aminothiophenol and a compound of Formula II, such as 5,6-dihydro-2H-pyran-2-one, all of which are either commercially available or may be readily prepared by known methods. The mixture can be dissolved in an appropriate non-polar solvent like methylene chloride and then heated in refluxing xylene to obtain the corresponding compound of Formula III. The compound of Formula III can be alkylated under basic conditions (such as with potassium carbonate or NaH) to yield the corresponding compound of Formula IV, such as by treatment with an alkylating agent including but not limited to substituted benzyl bromide or chlorides in refluxing acetone, dimethylformamide (DMF), or tetrahydrofuran (THF).

Alternatively, the compound of Formula III can be treated with an appropriate reducing agent such as diborane or lithium aluminum hydride in an appropriate solvent such as tetrahydrofuran, ether or 1,4-dioxane to obtain the corresponding compound of Formula V. The compound of Formula V can be alkylated or acylated preferably at a temperature in the range of 0–60° C. to form the corresponding compound of Formula VI, such as by adding either substituted benzyl, substituted benzene sulfonyl, or phenacyl halides to a solution of the corresponding compound of Formula V in tetrahydrofuran, ether or methylene chloride pretreated with N,O-bis(trimethylsilyl)acetamide.

Compounds of Formulae IV and VI wherein $R^{2'}$ is nitro or acetamide can be converted to substituted anilines via standard procedures such as catalytic hydrogenation or acid treatment. The aniline can then be further substituted with a variety of substituted phenacyl halides in an appropriate solvent such as methylene chloride or THF and a base such as triethylamine once treated with N,O-bis(trimethylsilyl)acetamide to form the corresponding compounds of 'Formula Ia wherein $R^2$ is —N(H)Y$R^3$ or —YN(H)$R^3$.

The compounds of Formulae IV and VI can be alkylated, acylated, or oxidized to form compounds of Formula Ia. Alkylation or acylation at the hydroxyl position can be accomplished by the addition of an alkyl or acylhalide in the presence of a base such as sodium hydride, potassium hydride or triethylamine in an appropriate solvent such as THF, DMF or methylene chloride. Phenyl or substituted phenyl ethers can be formed by the addition of phenol or substituted phenols to compound of Formulae IV and VI using triphenylphosphine and diethyl azodicarboxylate in a solvent such as tetrahydrofuran. Oxidation can be executed by using oxidizing agents such as pyridinium chlorochromate, pyridinium dichromate or Jones reagent using known procedures for this transformation.

To make compounds of Formula I wherein $R^1$ is o-mesylate, —SO$_2$OH, alkoxysulfonyl, alkoxycarbonyl, substituted alkoxycarbonyl, —NR$^4$R$^5$, —OH, cyano, N-morpholino, —NHCOR$^6$ or —CONR$^7$R$^8$, the compounds of Formula III or V may be used as the starting material and can be further converted to the corresponding compounds of Formula I or VIII according to Scheme 2.

Scheme 2

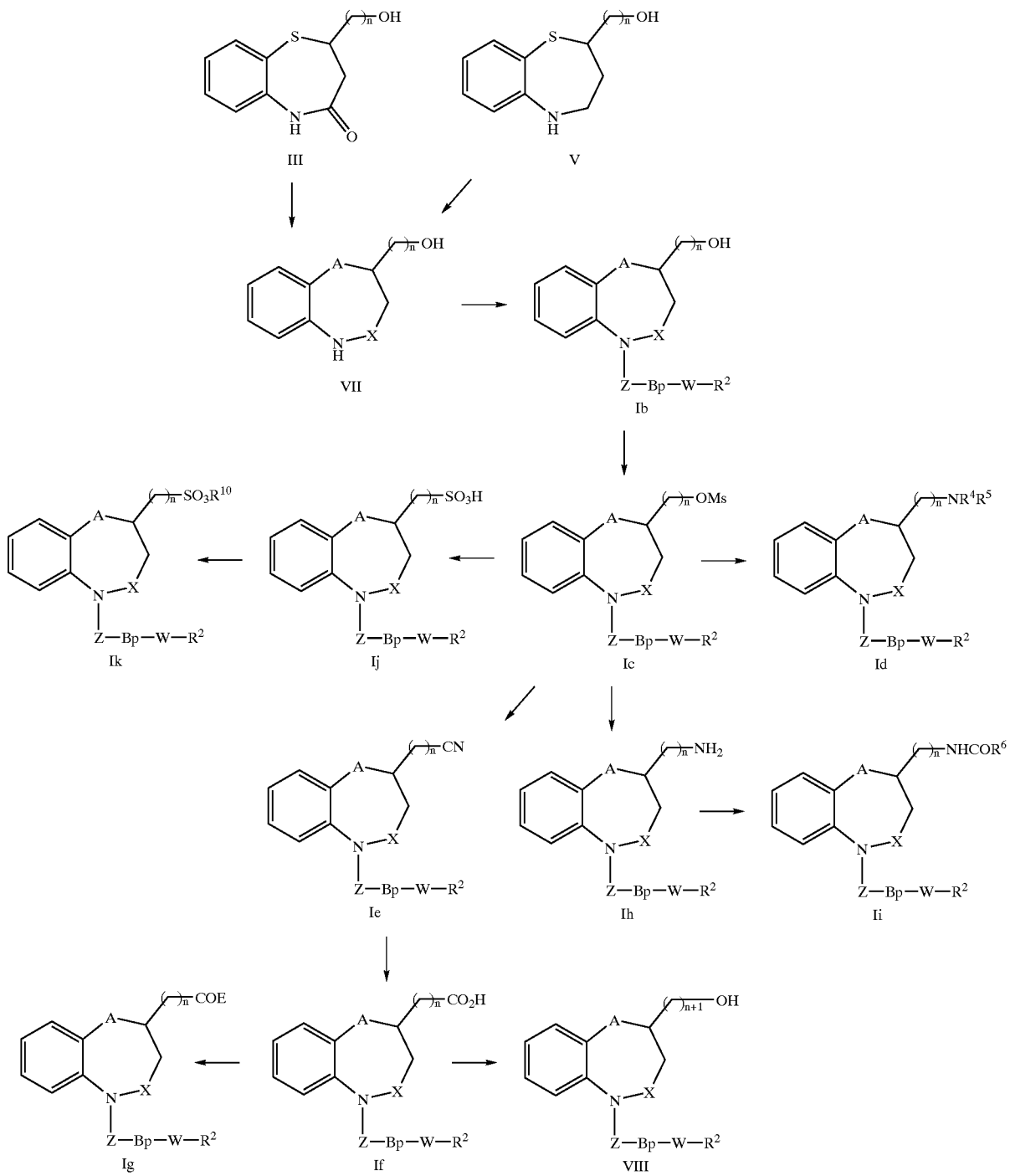

As set forth in Scheme 2, wherein E is —NR$^7$R$^8$ or —OR$^{10}$, R$^{10}$ is alkyl or substituted alkyl, and A, X, Z, Bp, W, R$^2$, R$^7$, R$^8$, n are as described above, the intermediates (III and V) may be oxidized to form the corresponding compounds of Formula VII using oxidizing agents such as 3-chloroperoxybenzoic acid in an appropriate solvent such as methylene chloride. Alkylation or acylation on the ring nitrogen of Formula VII can be achieved preferably at a temperature in the range of 0–60° C. to form the corresponding compound of Formula Ib, such as by adding either substituted benzyl, or phenacyl halides to a solution of the corresponding compound of Formula VII in tetrahydrofuran, ether or methylene chloride pretreated with N,O-bis (trimethylsilyl)acetamide.

The hydroxyl group in the compound of Formula Ib can be converted under basic conditions such as TEA to the mesylate in the compound of Formula Ic. The mesylate can then be displaced with a variety of substituted amines or morpholine preferably at a temperature between 60 and 80° C. in an appropriate solvent such as tetrahydrofuran or dimethylformamide to give compounds of the Formula Id. The mesylate can also be heated under similar conditions with ammonium hydroxide to afford compounds of the Formula Ih which can be further functionalized by treatment with substituted acylhalides and triethylamine in non-polar solvents such as THF or methylene chloride to give the corresponding compounds of the Formula Ii.

Alternatively, the mesylate of Formula Ic can be treated with sodium cyanide in an appropriate solvent such as dimethylformamide to give the compound of Formula Ie. The compound of Formula Ie can be further hydrolyzed to form the compound of Formula If under basic conditions such as NaOH. An alternative way to extend the $CH_2$ chain connecting $R^1$ is reduction of the compound of Formula If with an appropriate reducing agent such as lithium alumiresolved into the optical antipodes by known methods, such as chiral HPLC methods, conversion and separation of diastereomeric salts, or formation and separation of diastereomeric esters or carbamates. As exemplified in Scheme 3 below, wherein compounds of Formula II may be made according to Schemes 1 and/or 2 and (*) represents a stereogenic center, the diastereomeric carbamates of Formula Im can be formed by the addition of a chiral auxiliary such as (S)-(−)-1-phenylehtylisocyanate to the starting substituted benzothiazepine of Formula II in refluxing toluene. Once separated by column chromatography each pure diastereomer can be hydrolyzed under basic conditions (sodium ethoxide) to obtain each enantiomer of Formulae In and Ip in pure form.

Scheme 3

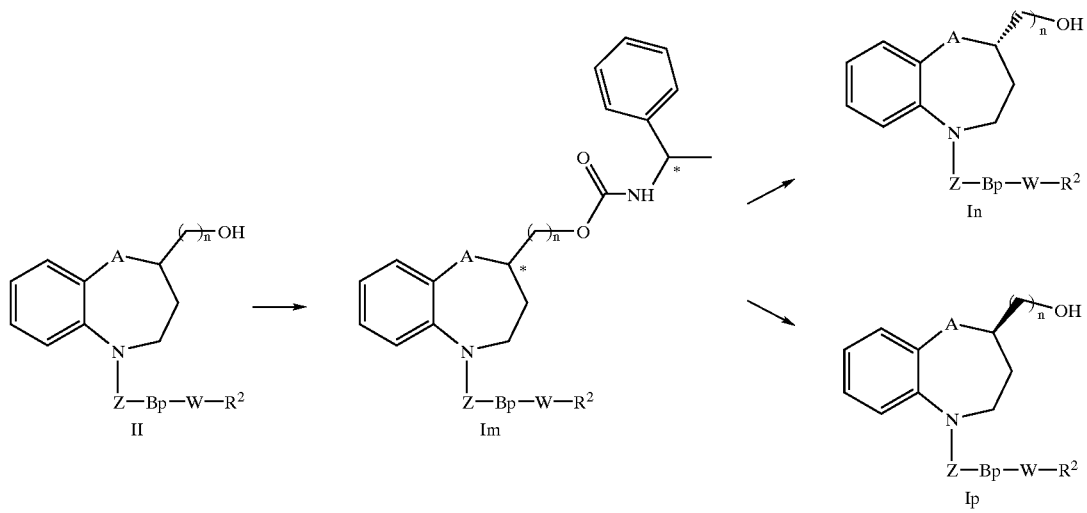

num hydride (LAH) to obtain the compound of Formula VIII, which can then be used in place of Ib for making the compounds of Formulae Ic–Ik.

Esters of Formula Ig can be prepared by treating the carboxylic acids of Formula If with an alkylhalide under basic conditions (such as with NaH or potassium carbonate) in dimethylforamide or tetrahydrofuran. The unsubstituted amides of Formula Ig can be prepared by treating the carboxylic acids of Formula If with di-tert-butyl dicarbonate, ammonium hydrogen carbonate and pyridine in a suitable solvent such as dioxane. Substituted amides of Formula Ig can be obtained by forming the acid chlorides of Ig using thionylchloride as the reagent. The acid chloride can then be reacted with substituted amines.

Alternatively, the mesylate of Formula Ic can also be converted to a bromide using a metal halide such as lithium, potassium, or sodium bromide in dry tetrahydrofuran, dimethylforamide or acetonitrile. This can then be converted to the sulfonic acid in the compound of Formula Ij by treating the bromide with sodium sulfite in an appropriate solvent such as ethanol/water. The sulfonic acids can be converted to sulfonyl chlorides by treatment with thionyl chloride or phosphorous pentachloride followed by treatment with an alkanol using a base such as pyridine under known conditions to give the corresponding compounds of Formula Ik.

The compounds of this invention exist in a racemic form as well as (−) and (+) enantiomers. The racemate can be The method of treating vascular resistance disorders described in the present invention may also be carried out using a pharmaceutical composition comprising any of the compounds as defined herein and a pharmaceutically acceptable carrier. The pharmaceutical composition may contain between about 100 mg and 1000 mg, preferably about 100 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms can be in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders of vascular resistance is required.

The daily dosage of the products may be varied over a wide range from 100 to 1000 mg per adult human per day. For oral administration, the compositions are preferably provided in the form of tablets containing the active ingredient in the amount sufficient for the symptomatic adjustment of the dosage to the patient to be treated. An effective amount of the drug is ordinarily supplied at a dosage level of from about 1 mg/kg to about 30 mg/kg of body weight per day. Preferably, the range is from about 3 to about 15 mg/kg of body weight per day, most preferably, from about 5 to about 10 mg/kg of body weight per day. The compounds may be administered on a regimen of 1 to 2 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following examples are intended to illustrate the invention but not to limit it.

EXAMPLE 1

2-(2-Hydroxyethyl)-benzothiazepin-4-one

2-Aminothiophenol (51 g, 410 mmol) and 5,6-dihydropyran-2-one (40 g, 410 mmol) were combined with triethylamine (1 ml) in $CH_2Cl_2$ (500 ml) causing an exothermic reaction that was allowed to cool to room temperature (RT). The mixture was stirred at room temperature for two days. The reaction was washed with dilute $NH_4Cl$ then with brine and dried over $Na_2SO_4$. The volatiles were removed in vacuo. The resulting yellow oil (91 g) was diluted with xylene (500 ml) and stirred at reflux for 5 days, chilled and the resulting light brown crystals, collected by filtration. 52 g, 61% . mp 173–175° C. $^1$H NMR (300 MHz, $CDCl_3$) 9.66 (broad s, 1H), 7.60–6.85 (m, 4H), 4.45 (t, 1H), 3.77 (m, 1H), 3.67–3.13 (m, 2H), 2.63–2.00 (m, 2H), 1.90–1.53 (m, 2H); IR (KBr) 3400, 2200, 1600 $cm^{-1}$; MS: m/z $(MH^+)$224

EXAMPLE 2

2-(2-Hydroxyethyl)-1,5-benzothiazepine

A borane THF solution (1M solution; 600 ml) was slowly added to a cooled (0° C.) solution of 2-(2-hydroxyethyl)-benzothiazepin-4-one as prepared in Example 1 (50 g, 0.22M)in dry THF (500 ml). The ice bath was removed and the mixture was stirred at reflux overnight then allowed to cool to room temperature. The mixture was cooled in an ice bath and quenched with 1N NaOH. The THF was removed under reduced pressure and the aqueous mixture extracted with ethyl acetate (EtOAc) (2×300 ml). The combined EtOAc extracts were washed with brine, dried (MgSO4), filtered and evaporated in vacuo to give a yellow oil. $^1$H NMR (300 MHz, CDCl3) δ7.36 (d, 1H); 7.046 (t, 1H); 6.766 (t, 1H); 6.725 (d, 1H); 4.413 (s, 1H); 3.915–3.773 (m, 2H); 3.646–3.57 ( m, 1H); 3.317–3.227 (m, 1H); 3.119–3.051 (m, 1H), 2.248–2.186 (m, 1H); 1.934–1.789 (m, 1H). MS: m/z $(MH^+)$ 210.

EXAMPLE 3

2-(2-Hydroxyethyl)-5-(4-(2-phenylbenzoylamino) benzoyl)-1,5-benzothiazepine (Compound 17)

A mixture of 2-biphenylcarboxylic acid (25 g, 0.13M) in thionyl chloride (80 ml) was stirred at room temperature overnight and the excess $SOCl_2$ removed under reduced pressure to give the acid chloride as a yellow oil. The oil was dissolved in methylene chloride (60 ml) and slowly added through an addition funnel to a solution of methyl(4-amino) benzoate (20 g, 0.13M) and triethylamine (28 ml, 0.198M) dissolved in methylene chloride (400 ml). The resulting mixture was stirred at room temperature for 4–5 hours and water (500 ml) was added. Layers were separated, the $CH_2Cl_2$ layer dried ($MgSO_4$) and solvent removed under reduced pressure. The resulting solids were washed with diethyl ether and dried to give a tan solid benzyl ester (37 g, 89%). M.P. 160–161° C. To a stirred solution of the ester (37 g, 0.11M) in CH3OH (400 ml) was slowly added 6.6N NaOH (100 ml). Stirring was continued till all solids dissolved (6 hours). The methanol was removed under reduced pressure, the solids dissolved in $H_2O$ and concentrated HCl was slowly added to the stirred solution. The mixture was stirred at RT overnight and the resulting white solid precipitates collected and dried to give the desired p-substituted benzoic acid as a white crystalline solid (34.4 g, 97%). MS: m/z (M$^+$) 318. The acid chloride was prepared by stirring the acid (34 g, 0.1M) in thionyl chloride (260 ml) with gentle heating (40° C. oil bath) for 4 hours. The residual semi solid was diluted with toluene and filtered to give the acid chloride product as white solid (33.6 g, 93.5%). M.P. 148–150° C. To a cold (ice bath) solution of 2-(2-hydroxyethyl)-1,5-benzothiazepine as prepared in Example 2, (17 g, 0.082M) an dry THF (100 ml) was slowly added N,O-bis (trimethylsilyl)acetamide (36 ml, 0.16M). The resulting mixture was stirred at room temperature for 1.5 hr and the prepared 4-(2-phenylbenzoylamino)-benzoylchloride (27 g, 0,082M) dissolved in methylene chloride was slowly added through an additional funnel over a 45 min. period. Stirring was continued for an additional two hours and H$_2$O was slowly added. The aqueous mixture was stirred overnight and the resulting solid precipitates were collected by filtration and dried to give the desired substituted benzothiazepine product(35.4 g, 85%). M.P. 224–228° C. Compound exists as a pair of rotamers. $^1$H NMR (300 MHz, DMSOd$_6$) δ10.26(s,1H); 7.62–6.88 ( m, 18H), 4.85, 4.54 (m, 2H); 3.59 (m, 2H); 3.07, 2.96, 2.14 (m, 2H); 2.27, 2.14 (m 1H); 1.94 (m, 1H); 1.76 (m, 1H); 1.54 (m, 1H). MS: m/z (MH$^+$) 509.

EXAMPLE 4

2-Carboxymethyl-5-(4-(2-phenylbenzolylamino) benzoyl)-1,5-benzothiazepine (Compound 29)

Pyridinium dichromate (38 g, 0.1M) was slowly added to a solution of Compound 17 as prepared in Example 3 (10.2 g, 0.02M) in dimethylformamide (50 ml). The resulting mixture was stirred at room temperature for 4–6 hours and diluted with methylene chloride (200 ml). The mixture was stirred at room temperature for 30 minutes and filtered through a short column (EM silica gel 60/Celite) eluting further with methylene chloride then ethyl acetate. The solvents were removed under reduced pressure to give a crude semi-solid. Flash column chromatography (EM silica gel 60; 5% MeOH in CH$_2$Cl$_2$) followed by recrystallization, gave pure product as a white solid (9.2 g, 88%). M.P. 204–208° C. Compound exists as a pair of rotamers. $^1$H NMR (400 MHz, DMSOd$_6$) δ10.29 (s,1H) ; 7.52–7.07 (m, 18H); 6.90 (m, 1H); 4.83, 4.62 (m, 1H) ; 3.55, 3.30 (m, 1H) ; 2.99, 2.78 (m, 1H) ; 2.63, 2.52 (m, 1H) ; 2.46, 2.37 (m, 1H); 2.24, 2.13 (m, 1H); 1.99, 1.88 (m, 1H). m/z (MH$^+$) 523.

EXAMPLE 5

2-Carboxymethyl-1-oxo-5-(4-(2-phenylbenzoylamino)benzoyl)-1,5-benzothiazepine (Compound 24)

Excess Jones reagent (5.0 ml) prepared by a slow addition of concentrated sulfuric acid (150 ml) to a cold solution (0–5° C.) of CrO$_3$ (180 g, 1.8M) in ice water (1.21) and stirred for one hour at 0° C., was slowly added to a cold mixture of Compound 17 as prepared in Example 3 (4.0 g, 7.8 mM) in acetone (60 ml). The resulting mixture was stirred at room temperature overnight. Water (100 ml) was then slowly added and the volatile solvents removed in vacuo. The aqueous mixture was extracted with ethyl acetate (2×100 ml). The combined EtOAc extracts were dried (MgSO$_4$), filtered and evaporated in vacuo to give a crude product. Purification by flash column chromatography (EM silica gel 60; 10% EtOAc in CH$_2$Cl$_2$) gave the desired product as a white solid. m/z (MH$^+$) 539.

EXAMPLE 6

2-(2-Methanesulfonylethyl)-5-(4-nitrobenzoyl)-1,5-benzothiazepine

Methanesulfonyl chloride (1.8 ml, 23 mM) was slowly added to a cold solution of 2-(2-hydroxyethyl)-1,5-benzothiazepine as prepared in Example 2 (5 g, 23 mM) and triethylamine (6.6 ml, 47 mM) in methylene chloride (10 ml). The mixture was stirred at 0° C. for three hours then poured into ice water (100 ml). The layers were separated and the methylene chloride layer dried (MgSO$_4$) . Once filtered, the solution containing the desired mesylate product was treated with triethylamine (4.8 ml, 34 mM) then with 4-nitrobenzoylchloride (4.2 g, 23 mM). The mixture was stirred at room temperature overnight, poured into water (150 ml) and layers were separated. The methylene chloride was dried (MgSO$_4$), evaporated in vacuo and purified by column chromatography to give the desired product (8.7 g, 86%). m/z (MH$^+$) 437

EXAMPLE 7

2-(2-Dimethylaminoethyl)-5-(4-aminobenzoyl)-1,5-benzothiazepine (Compound 12)

A mixture of 2-(2-methanesulfonylethyl)-5-(4-nitrobenzoyl)-1,5-benzothiazepine as prepared in Example 6 (0.9 g, 2.1 mM) and dimethylamine (40% solution in water, 3.0 ml) in tetrahydrofuran (10 ml) was heated in a sealed tube with stirring in an 80° C. oil bath for 16 hours. The mixture was cooled to room temperature, evaporated to dryness, diluted with water (30 ml) and extracted with ethyl acetate (2×35 ml). The combined ethyl acetate extracts were dried (MgSO$_4$) and evaporated in vacuo to give the desired product (0.78 g, 97%). This product (0.78 g, 2.0 mM) was dissolved in ethanol, and a catalytic amount of 10% Pd/C was added. The mixture was hydrogenated in a PARR apparatus under 30 psi of H$_2$ pressure for 16 hr, filtered through Celite and evaporated in vacuo to give the desired product (0.64 g, 90%). m/z (M$^+$) 356.

EXAMPLE 8

2-(2-Dimethylaminoethyl)-5-(4-(2-phenylbenzoylamino)benzoyl)-1,5-benzothiazepine (Compound 11)

2-Phenylbenzoyl chloride (0.36 g, 1.67 mM)(prepared from 2-biphenylcarboxylic acid as described in Example 3) was slowly added to a solution of Compound 12 as prepared in Example 7 (0.5 g, 1.4 mM) and triethylamine (0.38 ml, 3.3 mM)in methylene chloride (30 ml). The mixture was stirred at room temperature for 16 hours and water (80 ml) was added. The layers were separated. The methylene chloride layer was dried (MgSO$_4$), filtered and evaporated in vacuo to give a crude product. Purification by flash column chromatography (EM silica gel 60; 30% EtOAc in CH$_2$Cl$_2$) yielded the desired product as a white solid. m/z (MH$^+$) 536.

EXAMPLE 9

2-(2-Dimethylaminoethyl)-5-[4-(2-methylbenzoylamino)benzoyl]-1,5-benzothiazepine (Compound 9)

Compound 12 as prepared in Example 7 (0.118 mg, 0.37 mM) was treated following the procedure of Example 8, with 2-toluoyl chloride (0.04 ml, 0.33 mM) substituted for 2-phenylbenzoyl chloride, to give a white solid product. m/z (MH$^+$) 474.

EXAMPLE 10

2-(2-Methanesulfonylethyl)-5-(4-(2-methylbenzoylamino)benzoyl)-1,5-benzothiazepine (Compound 13)

2-(2-Methanesulfonylethyl)-5-(4-nitrobenzoyl)-1,5-benzothiazepine as prepared in Example 6 (0.3 g, 0.68 mM)

was dissolved in ethanol, and a catalytic amount of 10% Pd/C was added. The mixture was hydrogenated in a PARR apparatus under 30 psi of $H_2$ pressure for 16 hr, filtered through Celite, evaporated in vacuo, then treated with as described in Example 8 with 2-toluoyl chloride substituted for 2-phenylbenzoyl chloride to give the desired mesylate product as a white solid (0.22 g, 56%). m/z ($MH^+$) 525.

EXAMPLE 11

2-(2-Methanesulfonylethyl)-5-[(4-(2-phenylbenzoylamino)benzoyl)]-1,5-benzothiazepine (Compound 16)

2-(2-Methanesulfonylethyl)-5-(4-nitrobenzoyl)-1,5-benzothiazepine as prepared in Example 6 was dissolved in ethanol, and a catalytic amount of 10% Pd/C was added. The mixture was hydrogenated in a PARR apparatus under 30 psi of $H_2$ pressure for 16 hr, filtered through Celite, evaporated in vacuo, then treated as described in Example 8 to give the desired mesylate as a white solid. m/z ($MH^+$) 587.

EXAMPLE 12

2-(2-Methylaminoethyl)-5-[4-(2-methylbenzoylamino)benzoyl]-1,5-benzothiazepine (Compound 14)

Compound 13 as prepared in Example 10 (0.045 g, 0.08 mM) and methylamine (40% solution in water; 1 ml) in tetrahydrofuran (4 ml) was heated in a sealed tube with stirring in an 80° C. oil bath for 16 hours. The mixture was cooled to room temperature, evaporated to dryness, diluted with water (30 ml) and extracted with ethyl acetate (2×35 ml). The combined ethyl acetate extracts were dried ($MgSO_4$) and evaporated in vacuo to give a crude mixture. Purification by chromatography (EM silica Gel 60; 10% EtOAc in $CH_2Cl_2$) gave the product as a white solid. m/z ($MH^+$)460.

EXAMPLE 13

2-(2-Aminoethyl)-5-[4-(2-methylbenzoylamino)benzoyl]-1,5-benzothiazepine (Compound 15)

A mixture of Compound 13 as prepared in Example 10 (0.050 g, 0.09 mM) in tetrahydrofuran (4 ml) was treated as described in Example 12 with ammonium hydroxide (1 ml) substituted for dimethylamine to give a white solid product. m/z ($MH^+$)446

EXAMPLE 14

2-(2-Aminoethyl)-5-[4-(2-phenylbenzoylamino)benzoyl]-1,5-benzothiazepine (Compound 28)

Compound 16 as prepared in Example 11 was treated as described in Example 13 to give a white solid product. m/z ($MH^+$)508.

EXAMPLE 15

2-[2-Amino-2-methyl propionamido]-ethyl-5-[4-(2-phenylbenzoylamino)benzoyl]-1,5-benzothiazepine Hydrochloride (Compound 39)

A mixture of Compound 28 as prepared in Example 14 (0.180 g, 0.36 mM), 2-(tert-butoxycarbonylaminoisobutyric acid (0.072 g, 0.36 mM), 1-hydroxybenzotriazole (0.05 g, 0.36 mM) and 1-[3-(dimethyamino)propyl]-3-ethylcarbodiimide hydrochloride (0.169 g, 0.9 mM) in methylene chloride (30 ml) was stirred at room temperature for 6 hours and a saturated potassium carbonate solution was added. Water was added and the layers were separated. The methylene chloride layer was dried ($MgSO_4$), evaporated in vacuo and the resulting semi-solid purified by chromatography. The BOC group was removed with trifluoroacetic acid to give the desired amine. The HCl salt was prepared and recrystallized from methanol/diethyl ether to give the desired product as a white crystalline solid. m/z ($MH^+$)593.

EXAMPLE 16

2-[5-[4-(2-Phenylbenzoylamino)benzoyl]-1,5-benzothiazepine]acetaldehyde (Compound 25)

A mixture of Compound 17 as prepared in Example 3 (0.24 g, 0.47 mM), Celite and pyridinium chlorochromate (0.2 g, 0.90 mM) in methylene chloride (30 ml) was stirred at RT overnight, filtered through Celite. The methylene chloride was removed under reduced pressure and the residue chromatographed (EM silica gel 60; 30% EtOAc in $CH_2Cl_2$) to give the title product (160 mg, 67%). m/z ($MH^+$)507

EXAMPLE 17

2-(2-Cyanoethyl)-5-[4-(2-phenylbenzoylamino)benzoyl]-1,5-benzothiazepine (Compound 30)

A mixture of Compound 16 as prepared in Example 11 (0.115 g, 0.197 mM) and sodium cyanide (20 mg) in dimethylformamide was stirred in a 70° C. oil bath for 4 hours. The reaction mixture was then cooled to RT and the DMF was removed under reduced pressure. The residual semi-solid was diluted with water (30 ml) and extracted with ethyl acetate (2×30 ml). The combined ethyl acetate extracts were dried ($MgSO_4$), filtered and evaporated in vacuo. The crude mixture was purified by chromatography to give pure product as a white solid (71 mg, 70%). m/z ($MH^+$)518

EXAMPLE 18

2(2Carboxyethyl)-5-[4-(2-phenylbenzoylamino)benzoyl]-1,5-benzothiazepine (Compound 31)

A 6.6N NaOH solution (0.5 ml) was added to a mixture of Compound 30 as prepared in Example 17 (0.05 g, 0.096 mM) in methanol. The mixture was stirred at reflux overnight, cooled to room temperature and evaporated in vacuo. The residue was diluted with water and enough 6N HCl was added drop-wise to precipitate the product. The solid product was collected by filtration and dried. m/z ($MH^+$)537

EXAMPLE 19

2-Ethyl[5-[4-(2-phenylbenzoylamino)benzoyl]-1,5-benzothiazepin]sulfonic Acid (Compound 32)

A mixture of Compound 16 as prepared in Example 11 (0.31 g, 0.5) and lithium bromide (46 mg) in dry tetrahyrofuran (30 ml) was stirred at reflux for 6 hours, cooled to room temperature and evaporated in vacuo. The residue was diluted with water and extracted with ethyl acetate. The ethyl acetate extract was dried ($MgSO_4$), filtered and evaporated in vacuo to give the bromide. The bromide was diluted with an ethanol/water mixture (20/10) and treated with two equivalence of sodium sulfite. The mixture was stirred at reflux for 16 hours, cooled to room temperature and the ethanol was removed under reduced pressure. Another 30 ml of water was added then 2N HCl. The aqueous mixture was extracted with ethyl acetate (2×50 ml). The ethyl acetate extracts were dried (MgSO$_4$) filtered and evaporated in vacuo. The crude semi-solid was chromatographed (EM silica gel 60; 10% MeOH in CH$_2$Cl$_2$) to give the product. m/z (MH$^+$)573

EXAMPLE 20

2-Acetamido-5-[4-(2-phenylbenzoylamino)benzoyl]-1,5-benzothiazepine (Compound 38)

Ammonium hydrogen carbonate (0.029 g, 0.36 mM) was added to a mixture of Compound 29 as prepared in Example 4 (0.160 g, 0.31 mM), di-tert-butyl dicarbonate (0.078 g, 0.36 mM) and pyridine (0.2 ml) in dioxane (10 ml). The mixture was stirred at room temperature overnight and water was added. The precipitates were collected and dried to give a white solid product (0.11 g,68%) m/z (MH$^+$)522

EXAMPLE 21

2-(2-Hydroxyethyl)-5-(4-aminobenzyl)-1,5-benzothiazepine-4-one

A mixture of 2-(2-hydroxyethyl)-benzothiazepin-4-one as prepared in Example 1 (3 g, 13.5 mM), potassium carbonate and p-nitrobenzyl bromide (3.0 g, 13.8 mM) in acetone (100 ml) was stirred at reflux for 48 hours, cooled to room temperature, diluted with water (80 ml) and evaporated in vacuo to remove the acetone. The aqueous mixture was extracted with ethyl acetate (2×80 ml. The combined organic extracts were dried (MgSO$_4$), filtered and evaporated in vacuo to give the desired product as an oil (4.2 g, 87.5%). m/z (M$^+$) 359. The oil (1.2 g, 3.4 mM) was dissolved in ethanol and a 5 mole % of 10% Pd/C was added. The mixture was hydrogenated under H$_2$ pressure in a Parr apparatus for 16 hours, filtered through Celite and evaporated in vacuo to give the desired product (1.1 g, 100%) as an oil. m/z (MH$^+$) 329.

EXAMPLE 22

2-(2-Hydroxyethyl)-5-(4-(2-phenylbenzoylamino) benzyl)-1,5-benzothiazepine-4-one (Compound 23)

To a cold (ice-bath) solution of 2-(2-hydroxyethyl)-5-(4-aminobenzyl)-1,5-benzothiazepine-4-one as prepared in Example 21 (0.865 g, 2.6 mM) in dry THF was added N,O-bis(trimethylsilyl)acetamide (1.16 ml, 5.2 mM). After 1 hour, 2-phenylbenzoyl chloride (0.570 g, 2.6 mM), prepared from 2-biphenylcarboxylic acid as described in Example 3, was added and stirring was continued for an addition hour. Water (80 ml) was added and the mixture was extracted with ethyl acetate (2×80 ml). The organic extract was dried (MgSO$_4$), filtered and evaporated in vacuo to give a crude product. Purification by flash column chromatography (EM silica gel 60; 30% EtOAc in CH$_2$Cl$_2$) yielded the desired product as a white solid (1.1 g, 83%) m.p.116–120° C. $^1$H NMR (300 MHz, DMSOd$_6$) δ7.8 (d, J=7 Hz, 1H); 5.09(d, J=15 Hz, H); 4.89(d,J=15 Hz,1H); 3.79 (m, 3H); 2.69–2.24 (m, 2H); 1.71 (m, 2H); m/z (MH$^+$)509.

EXAMPLE 23

2-(2-Hydroxyethyl)-5-(4-(2-methylbenzoylamino) benzyl)-1,5-benzothiazepine-4-one (Compound 22)

2-(2-Hydroxyethyl)-5-(4-aminobenzyl)-1,5-benzothiazepine-4-one as prepared in Example 21 (0.105 g, 0.31 mM) was treated using the procedure described in Example 22, with o-toluoyl chloride (0.04 ml, 0.33 mM) substituted for 2-phenylbenzoyl chloride, to yield the title product as a white solid (0.086 g, 64%) m/z (MH$^+$) 447

EXAMPLE 24

2-(2-Hydroxyethyl)-5-(4-acetamidobenzenesulfonyl)-1,5-benzothiazepine

To a mixture of 2-(2-hydroxyethyl)-1,5-benzothiazepine as prepared in Example 2 (3 g, 14.4 mM) in pyridine (30 ml) was slowly added N-acetylsulfanilyl chloride (6.7 g, 28.7 mM). The resulting mixture was stirred at room temperature for 16 hours and the excess pyridine was removed under reduced pressure. The residual semi-solid was diluted with H$_2$O (80 ml) and extracted with CH$_2$Cl$_2$ (2×80 ml). The combined methylene chloride extracts were dried (MgSO$_4$), filtered and evaporated in vacuo to give a crude oil. Flash column chromatography (EM silica gel 60; 2% MeOH in CH$_2$Cl$_2$) gave the desired product as a white solid (2.9 g, 50%). m/z (MH$^+$)407

EXAMPLE 25

2-(2-Hydroxyethyl)-5-(4-aminobenzenesulfonyl)-1, 5-benzothiazepine (Compound 4)

2-(2-Hydroxyethyl)-5-(4-acetamidobenzenesulfonyl)-1, 5-benzothiazepine as prepared in Example 24 was dissolved in a 10% HCl/MeOH (100 ml) solution and stirred at reflux for 2½ hours. The mixture was cooled and a saturated NaHCO$_3$ solution 160 ml) was added. The methanol was removed under reduced pressure and the aqueous mixture extracted with EtOAc (2×80 ml). The combined EtOAc extracts were dried (MgSO$_4$), filtered and evaporated in vacuo to give the desired product as a solid (2.4 g,92%) m.p. 145–148° C. $^1$H NMR (300 MHz, DMSOd6) 6 7.50( d, J=7 Hz, 1H); 7.41 (d, J=8.6 Hz, 2H); 7.33–7.19 (m, 3H); 6.59 (d, J=8.6 Hz, 2H); 6.05(s, 2H) 4.51 (t, J=5 Hz, 1H); 3.45–3.35 (m, 4H); 2.96 (m, 1H), 2.07(m, 1H); 1.81(m, 1H); 1.49(m, 2H) . m/z (MH$^+$) 365.

EXAMPLE 26

2-(2-Hydroxyethyl)-5-[4-(2-phenylbenzoylamino)-benzenesulfonyl]-1,5-benzothiazepine (Compound 19)

Compound 4 as prepared in Example 25 (0.6 g, 1.5 mM) was treated with N,O-bis(trimethylsilyl)acetamide (0.65 g, 3.0 ml) then with 2-phenylbenzoyl chloride (0.39 g,1.8 mM) as described in Example 22 to yield the title product as a white solid. m.p. $^1$H NMR (300 MHz, CDCl$_3$) δ7.92 (d, J=7.4 Hz, 1H); 7.60–7.04 (m, 17H); 3.76 (m, 2H); 2.89 (m, 1H); 2.08 (m, 1H); 1.90 (m, 1H); 1.64 (m, 4H). m/z (MH$^+$)545

EXAMPLE 27

2-(2-Hydroxyethyl)-5-[4-(2-methylbenzoylamino) benzene-sulfonyl]-1,5-benzothiazepine (Compound 5)

Compound 4 as prepared in Example 25 (0.55 g, 1.5 mM) was treated as described in Example 26 with 2-toluoyl chloride (0.3 ml) substituted for 2-phenylbenzoyl chloride to give the desired product m/z (MH$^+$)483

EXAMPLE 28

2-(2-Hydroxyethyl)-5-[4-(3,4-dichlorobenzoylamino)benzene-sulfonyl]-1,5-benzothiazepine (Compound 10)

Compound 4 as prepared in Example 25 was treated as described in Example 26 with 3,4-dichlorobenzoyl chloride (0.085 g, 0.41 mM) substituted for 2-phenylbenzoyl chloride to give the product. m/z (MH+)537

EXAMPLE 29

2-Ethyl-(2-methanesulfonyl)-1,5-benzothiazepine-4-one

Methanesulfonyl chloride (3.6 ml, 45 mM) was slowly added to a cooled (0° C.) solution of 2-(2-hydroxyethyl)-benzothiazepin-4-one as prepared in Example 1 (10 g, 45 mM) and triethylamine (4.5 ml, 32 mM) dissolved in methylene chloride. The mixture was stirred at room temperature for 1.5 hours, cooled in an ice bath and water was added. The aqueous mixture was extracted with ethyl acetate. The organic phase was dried ($MgSO_4$), filtered and evaporated in vacuo to give a solid product 14.1 g, 94%). m/z (MH+) 302

EXAMPLE 30

2-[N-(tert-butoxycarbonyl)-ethyl]-5-[4-(2-methylbenzoylamino)-benzyl]-1,5-benzothiazepine-4-one (Compound 6)

Sodium azide (5.9 g, 92 mM) was slowly added to a mixture of 2-ethyl-(2-methanesulfonyl)-1,5-benzothiazepine-4-one as prepared in Example 29 (14.0 g, 46.5 mM) in dimethylforamide (100 ml). The mixture was stirred at room temperature for fifteen minutes then heated in an 80° C. oil bath for an additional four hours. The mixture was cooled to room temperature, poured into ice water (300 ml) and stirred for one hour. The resulting precipitates were collected and dried to give the azide as an off-white solid (8.2 g, 72%). The azide (8.0 g, 32.2 mM) dissolved in dry tetrahydrofuran (60 ml) was added to a cooled solution of lithium aluminum hydride (48 ml; 1M solution in THF) in THF (100 ml). The mixture was stirred at room temperature for three hours and a saturated $K_2CO3$ solution was slowly added. The mixture was filtered through Celite and the THF was removed under reduced pressure. The resulting mixture was diluted with ethyl acetate (250 ml) and washed with water (1×250 ml) then with brine (1×250 ml). The ethyl acetate extract was dried($MgSO_4$), filtered and evaporated in vacuo to give the amine as a yellow oil (3.96 g, 56%). To a cold (0° C.) mixture of the amine (3.9 g, 17.8 mM) in dry THF (80 ml) was added di-tert-butyl dicarbonate (3.89 g, 17.8 mM). The mixture was slowly warmed up to room temperature, stirred for one hour. The mixture was again cooled in an ice-bath and water (80 ml) was added. The THF was removed under reduced pressure and the aqueous mixture extracted with ethyl acetate (2×80 ml). The combined ethyl acetate extracts were dried ($MgSO_4$), filtered, evaporated in vacuo. Purification by flash column chormatography (EM silica gel, 10% EtOAc in $CH_2Cl_2$) gave the desired product (3.7 g, 65%). Further treatment with 4-nitrobenzyl bromide, catalytic hydrogenation as described in Example 21 followed by acylation with o-toluoyl chloride as described in Example 23 gave the desired product as an off-white solid. m/z (MH+)540.

EXAMPLE 31

2-(2-Aminoethyl)-5-[4-(2-methylbenzoylamino)-benzyl]-1,5-benzothiazepine-4-one (Compound 7)

Compound 6 as prepared in Example 30 was dissolved in methylene chloride and treated with excess trifluoroacetic acid. The mixture was stirred at room temperature overnight and diluted with saturated sodium bicarbonate. The layers were separated and the methylene chloride layer dried ($MgSO_4$), filtered and evaporated in vacuo to give the desired product as a solid m/z (MH+) 446.

EXAMPLE 32

2-[2-(2,4-Dimethoxybenzylamino)ethyl]-5-[4-(2-methylbenzoylamino)-benzyl]-1,5-benzothiazepine-4-one (Compound 8)

A mixture of Compound 7 as prepared in Example 31 (0.105 g, 0.24 mM), 2,4-dimethoxybenzaldehyde (0.040 g, 0.240 mM) and acetic acid (0.05 ml) in methanol was stirred at room temperature for three hours and 2.5 equivalence of sodium cyanoborohydride was added. The mixture was stirred at room temperature for an additional 4 hours and a 6N NaOH (0.5 ml; adjusted to pH8) was added. The methanol was removed under reduced pressure and the residue diluted with water (50 ml) and extracted with ethyl acetate (2×5 ml). The ethyl acetate extracts were dried ($MgSO_4$), evaporated in vacuo and purified by flash column chromatography (EM silica gel 60; 5% MeOH in $CH_2Cl_2$) to give a white solid product. m/z (MH+) 596.

EXAMPLE 33

2-(2-Dimethylaminoethyl)-5-(4-acetamidobenzenesulfonyl)-1,5-benzothiazepine (Compound 1)

2-(2-Hydroxyethyl)-5-(4-acetamidobenzenesulfonyl)-1,5-benzothiazepine as prepared in Example 24 (1.2 g, 2.77 mM) was treated with triethylamine (0.6 ml) and methanesulfonyl chloride (0.2 ml, 3.05 mM) as described in Example 29 to give a yellow solid mesylate product. A mixture of the mesylate (0.20 g, 0.41 mM) and dimethylamine (40% in water solution; 3 ml)dissolved in tetrahydrofuran (4 ml) was heated in a sealed tube with stirring in an 80° C. oil bath for 16 hours. The mixture was cooled to room temperature, evaporated to dryness, diluted with water(30 ml)and extracted with ethyl acetate (2×35 ml). The combined ethyl acetate extracts were dried ($MgSO_4$) and evaporated in vacuo to give a solid product. m.p. 78–80° C. m/z (MH+) 434.

Example 34

2-(2-Hydroxyethyl)-5-[2-chloro-4-(2-methyl-5-fluorobenzoylamino)benzoyl]-1,5-benzothiazepine (Compound 43)

A mixture of 2-(2-hydroxyethyl)-1,5-benzothiazepine as prepared in Example 2 (0.070 g, 0.34 mM) and N,O-bis(trimethylsilyl)acetamide (0.15 ml, 0.67 mM)was treated as described in Example 3 with 2-Chloro-4-(2-methyl-5-fluorobenzoylamino)benzoyl chloride (0.11 g, 0.32 mM) substituted for 4-(2-phenylbenzoylamino)benzoyl chloride to give the product as a white solid. m/z (MH+) 500.

EXAMPLE 35

2-(2-Dimethylaminoethyl)-5-(4-(2-methylbenzoylamino)-benzenesulfonyl]-1,5-benzothiazepine (Compound 2)

2-(2-Dimethylaminoethyl)-5-(4-acetamidobenzenesulfonyl)-1,5-benzothiazepine as prepared in Example 33 was further treated as described in Examples 25 and 27 to give the desired product as an off-white solid m/z (MH+) 510.

EXAMPLE 36

2-[2-(N-Morpholino)-ethyl]-5-[4-(2-methylbenzoylamino)-benzenesulfonyl]-1,5-benzothiazepine (Compound 3)

2-(2-Hydroxyethyl)-5-(4-acetamidobenzene-sulfonyl)-1,5-benzothiazepine as prepared in Example 24 was treated as described in Example 33 with morpholine substituted for dimethylamine. Then the product was further treated as described in Examples 25 and 27 to give the product as a solid. m/z (MH$^+$) 552.

EXAMPLE 37

2-(2-Hydroxyethyl)-5-(4-(2-phenylbenzoylamino)-pyridinoyl)-1,5-benzothiazepine (Compound 40)

5-Carboxy-2-(2-methyl-5-fluorobenzoylamino)pyridine (0.66 g, 2.4mM) was treated with thionyl chloride then added to a mixture of 2-(2-hydroxyethyl)-1,5-benzothiazepine as prepared in Example 2(0.7 g, 3.3 mM) and N,O-bis(trimethylsilyl)acetamide (1.5 ml, 6.6 mM) in tetrahydrofuran and the solid product isolated. m/z (MH$^+$) 466

EXAMPLE 38

2-(2-Hydroxyethyl)-5-(4-(2-methylbenzoylamino)benzoyl)-1,5-benzothiazepine (Compound 18)

A mixture of 2-(2-hydroxyethyl)-1,5-benzothiazepine as prepared in Example 2 was treated as described in Example 3 with 2-toluoyl chloride substituted for 2-phenylbenzoylchloride to give the product as a white solid. m/z (MH$^+$) 447

EXAMPLES 39 and 40

2-(2-Hydroxyethyl)-1-dioxo-5-(4-(2-phenylbenzoylamino)-benzoyl)-1,5-benzothiazepine (Compound 35) and 2-(2-hydroxyethyl)-1-oxo-5-(4-(2-phenylbenzoylamino)-benzoyl)-1,5-benzothiazepine (Compound 36)

3-Chloroperoxybenzoic acid (0.34 g, 1.97 mM) was added to a mixture of Compound 17 as prepared in Example 3 (1.0 g, 1.97 mM) in methylene chloride. The mixture was stirred at RT overnight and an aqueous sodium sulfite solution was added. The layers were separated and the methylene chloride layer further extracted with saturated potassium carbonate, dried (MgSO$_4$), filtered and evaporated in vacuo to give a mixture of two products. Purification by chromatography (EM silica gel 60, 50% EtOAc in methylene chloride) give the sulfone product (0.650 g) and the sulfoxide product (0.43 g); m/z (MH$^+$) 541 and 525, respectively.

EXAMPLE 41

2-(2-Methanesulfonylethyl)-5-[(4-(2-phenylbenzoylamino)-benzyl)]-1,5-benzothiazepin-4-one (Compound 21)

Methanesulfonyl chloride (0.04 ml, 0.55 mM) was added to Compound 23 as prepared in Example 22 (0.280 g, 0.55 mM) and triethylamine (0.15 ml, 1.1 mM) following the procedure described in Example 29 to give the solid product. m/z (MH$^+$) 587.

EXAMPLE 42

2-(2-Methanesulfonylethyl)-5-[(4-(2-phenylbenzoylamino)-benzenesulfonyl)]-1,5-benzothiazepine (Compound 20)

Methanesulfonyl chloride (0.02 ml, 0.278 mM) was added to Compound 19 as prepared in Example 26 (0.151 g, 0.278 mM) and triethylamine (0.07 ml, 0.55 mM) following the procedure described in Example 29 to give the solid product. m/z (MH$^+$) 623.

EXAMPLE 43

2-Methyl-[5-(4-(2-phenylbenzoylamino)benzoyl)-1,5-benzothiazepine]acetate (Compound 37)

Methyl iodide (0.06 ml, 0.96 mM)was added to a mixture of Compound 29 as prepared in Example 4 (0.5 g, 0.96 mM) and potassium carbonate (0.26 g, 1.88 mM) in dimethyl formamide (10 ml). The mixture was stirred at room temperature overnight and slowly added to water (80 ml). The white solid precipitates were collected and dried to give the product. m/z (MH$^+$) 537.

EXAMPLE 44–47

Preparation of Enantiomers of 2-(2-Hydroxyethyl)-5-(4-(2-phenylbenzoylamino)benzoyl)-1,5-benzothiazepine (Compounds 26 and 27) and 2-Carboxymethyl-5-[4-(2-phenylbenzoylamino)benzoyl]-1,5-benzothiazepine (Compounds 33 and 34)

(S)-(—)-1-Phenylethyl isocyanate (2.6 ml) was added to a suspension of Example 3 (7.8 g, 15.4 mM) and a catalytic amount of N,N-dimethylethanolamine in toluene (150 ml). The resultant mixture was stirred at reflux for 48 hours, cooled to room temperature and filtered to remove un-reacted starting material. The filtrate was evaporated in vacuo and the residual semi-solid chromatographed (EM silica gel 60, 10% tert-butyl ethyl ether in methylene chloride) to give each diastereomer pure. Each single diastereomer was then dissolved in ethanol and added to a sodium ethoxide solution. The mixture was stirred a reflux overnight and cooled to room temperature. The ethanol was removed under reduced pressure, the mixture diluted with 1N HCl and extracted with ethyl acetate. The ethyl acetate extract was dried (MgSO$_4$) and filtered. Removal of the solvent under reduced pressure and drying of the resulting solid gave the pure enantiomers of Compounds 26 and 27. Each enantiomer was then treated following the procedure described in Example 4 to give the pure enantiomers of Compounds 33 and 34.

EXAMPLE 48

In-Vitro Binding Assay

Assay buffer is 50 mM Tris-Cl, 5 mM MgC12, 0.1% BSA (pH 7.5) containing 5 ug/ml of aprotinin, leupeptin, pepstatin, 50 ug/ml bacitracin, and 1 mM Pefabloc. H3 vasopressin is $^3$H-arginine-8-vasopressin (68.5 Ci/mmol, final concentration in assay is 0.65–0.75nM). Into wells of 96-well round bottom polypropylene plates are added buffer, test compound, membrane (containing cloned human V2 receptor), and H3 vasopressin. The reaction plates are allowed to sit at room temperature for one hour. The samples are filtered through Unifilter GF/C plates (presoaked in 0.3 polyethyleneimine). The plates are washed 5 times with cold physiological saline containing 0.05% Tween 20. After drying, the bottom of the filter plates are sealed and 0.025 ml of Microscint-20 is added to each filter. The top of the plate is sealed, and the plate is counted. Non-specific binding is determined by the addition of 1.25 uM arginine-8-vasopressin in those wells. %Inh. is $$\% \text{ inhibition} = 100 - 100 \times \frac{\text{peak response after drug}}{\text{peak response before drug}}$$

Example 49
Reversal of Vasopressin-Induced Hypertension in Rats

The anti-hypertensive activity of a compound may be assessed using an anesthetized model of vasopressin-induced hypertension. Male Long Evans, normotensive rats of between 350 and 450 g in body weight may be anesthetized with pentobarbital (35 mg/kg, ip) and maintained throughout the procedure with an ip infusion of 10 mg/kg/hr. Arginine vasopressin can be infused at 30 ng/kg/min, iv, to induce a stable hypertensive state (ca. 50 mmHg increase in mean arterial blood pressure). Compounds of interest can be administered in an ascending dose fashion and the maximum decrease in mean arterial blood pressure can be recorded. An $ED_{50}$ may be determined from the linear portion of the dose-response relationship for each animal.

This model can be modified slightly to assess the bioavailability of compounds of interest. Rather than dosing the animals iv in an ascending dose fashion, a single dose per animal cab be administered directly into the duodenum. The anti-hypertensive effects can be then monitored for 60 minutes and the maximum percent reversal can then be calculated.

Tables I and II below set forth the vasopressin receptor binding data of some compounds of the instant invention.

TABLE I

Iq

| Cpd No. | A | n | $R^1$ | $R^2$ | Z | X | Receptor Binding (% Inh. @ concentration in $\mu M$) V1a | V2 |
|---|---|---|---|---|---|---|---|---|
| 1 | S | 2 | $N(CH_3)_2$ | $NHCOCH_3$ | $SO_2$ | $CH_2$ | 14% @ 25 | 7% @ 25 |
| 2 | S | 2 | $N(CH_3)_2$ | $NHCO(2-CH_3)Ph$ | $SO_2$ | $CH_2$ | 29% @ 25 | 34% @ 25 |
| 3 | S | 2 | N-morpholine | $NHCO(2-CH_3)Ph$ | $SO_2$ | $CH_2$ | 47% @ 25 | 37% @ 25 |
| 4 | S | 2 | OH | $NH_2$ | $SO_2$ | $CH_2$ | 21% @ 10 | 20% @ 10 |
| 5 | S | 2 | OH | $NHCO(2-CH_3)Ph$ | $SO_2$ | $CH_2$ | 13% @ 10 | $0.76^1$ |
| 6 | S | 2 | NHBOC | $NHCO(2-CH_3)Ph$ | $CH_2$ | CO | 13% @ 10 | 22% @ 10 |
| 7 | S | 2 | NH2 | $NHCO(2-CH_3)Ph$ | $CH_2$ | CO | 10% @ 10 | 4% @ 10 |
| 8 | S | 2 | $NCH_2$-(2,4-$OCH_3$)Ph | $NHCO(2-CH_3)Ph$ | $CH_2$ | CO | 33% @ 10 | 32% @ 10 |
| 9 | S | 2 | $N(CH_3)_2$ | $NHCO(2-CH_3)Ph$ | CO | $CH_2$ | $1.5^1$ | 63% @ 10 |
| 10 | S | 2 | OH | $NHCO(3,4-Cl)Ph$ | $SO_2$ | $CH_2$ | 0% @ 10 | $2.10^1$ |
| 11 | S | 2 | $N(CH_3)_2$ | $NHCO(2-Ph)Ph$ | CO | $CH_2$ | 63% @ 10 | $0.43^1$ |
| 12 | S | 2 | $N(CH_3)_2$ | $NH_2$ | CO | $CH_2$ | 35% @ 10 | 6% @ 10 |
| 13 | S | 2 | $OSO_2CH_3$ | $NHCO(2-CH_3)Ph$ | CO | $CH_2$ | $0.30^1$ | $0.20^1$ |
| 14 | S | 2 | $NHCH_3$ | $NHCO(2-CH_3)Ph$ | CO | $CH_2$ | 50% @ 1 | 28% @ 1 |
| 15 | S | 2 | $NH_2$ | $NHCO(2-CH_3)Ph$ | CO | $CH_2$ | 42% @ 1 | 47% @ 1 |
| 16 | S | 2 | $OSO_2CH_3$ | $NHCO(2-Ph)Ph$ | CO | $CH_2$ | $1.20^1$ | $0.013^1$ |
| 17 | S | 2 | OH | $NHCO(2-Ph)Ph$ | CO | $CH_2$ | $0.097^1$ | $0.008^1$ |
| 18 | S | 2 | OH | $NHCO(2-CH_3)Ph$ | CO | $CH_2$ | $0.041^1$ | $0.048^1$ |
| 19 | S | 2 | OH | $NHCO(2-Ph)Ph$ | $SO_2$ | $CH_2$ | 34% @ 1 | 27% @ 1 |
| 20 | S | 2 | $OSO_2CH_3$ | $NHCO(2-Ph)Ph$ | $SO_2$ | $CH_2$ | 24% @ 1 | 6% @ 1 |
| 21 | S | 2 | $OSO_2CH_3$ | $NHCO(2-Ph)Ph$ | $CH_2$ | CO | 5% @ 0.1 | 1% @ 0.1 |
| 22 | S | 2 | OH | $NHCO(2-CH_3)Ph$ | $CH_2$ | CO | 54% @ 1 | 33% @ 1 |
| 23 | S | 2 | OH | $NHCO(2-Ph)Ph$ | $CH_2$ | CO | 33% @ 1 | 43% @ 1 |
| 24 | SO | 1 | COOH | $NHCO(2-Ph)Ph$ | CO | $CH_2$ | 0% @ 1 | $0.108^1$ |
| 25 | S | 1 | CHO | $NHCO(2-Ph)Ph$ | CO | $CH_2$ | 30% @ 1 | $0.014^1$ |
| 26 | S | 2 | $OH^2$ | $NHCO(2-Ph)Ph$ | CO | $CH_2$ | $0.027^1$ | $0.007^1$ |
| 27 | S | 2 | $OH^2$ | $NHCO(2-Ph)Ph$ | CO | $CH_2$ | $0.091^1$ | $0.014^1$ |
| 28 | S | 2 | $NH_2$ | $NHCO(2-Ph)Ph$ | CO | $CH_2$ | 19% @ .1 | 46% 0.1 |
| 29 | S | 1 | COOH | $NHCO(2-Ph)Ph$ | CO | $CH_2$ | 16% @ .1 | $0.004^1$ |
| 30 | S | 2 | CN | $NHCO(2-Ph)Ph$ | CO | $CH_2$ | 34% @ .1 | $0.069^1$ |
| 31 | S | 2 | COOH | $NHCO(2-Ph)Ph$ | CO | $CH_2$ | 30% @ .1 | $0.009^1$ |
| 32 | S | 2 | $SO_3H$ | $NHCO(2-Ph)Ph$ | CO | $CH_2$ | 10% @ .1 | $0.012^1$ |
| 33 | S | 1 | $COOH^2$ | $NHCO(2-Ph)Ph$ | CO | $CH_2$ | 7% @ .1 | $0.008^1$ |
| 34 | S | 1 | $COOH^2$ | $NHCO(2-Ph)Ph$ | CO | $CH_2$ | 12% @ .1 | $0.007^1$ |

TABLE I-continued

Iq

| Cpd No. | A | n | R¹ | R² | Z | X | Receptor Binding (% Inh. @ concentration in μM) V1a | V2 |
|---|---|---|---|---|---|---|---|---|
| 35 | SO₂ | 2 | OH | NHCO(2-Ph)Ph | CO | CH₂ | 2% @ .1 | 20% @ .1 |
| 36 | SO | 2 | OH | NHCO(2-Ph)Ph | CO | CH₂ | 0 @ .1 | 38% @ .1 |
| 37 | S | 1 | CO₂CH₃ | NHCO(2-Ph)Ph | CO | CH₂ | 17% @ .1 | 0.050[1] |
| 38 | S | 1 | CONH₂ | NHCO(2-Ph)Ph | CO | CH₂ | 2% @ .1 | 0.024[1] |
| 39 | S | 1 | NCOC(CH₃)₂NH₂ | NHCO(2-Ph)Ph | CO | CH₂ | 0 | 0.017 |

TABLE II

Ir

| No. | A | n | R¹ | R² | Z | X | Receptor Binding (% Inh. @ concentration in μM) V1a | V2 |
|---|---|---|---|---|---|---|---|---|
| 40 | S | 2 | OH | NHCO(2-CH₃,5-F)Ph | CO | CH₂ | 22% @ .1 | 0.030[1] |
| 41 | S | 2 | OH | NHCO(2-Ph)Ph | CO | CH₂ | — | — |
| 42 | S | 1 | COOH | NHCO(2-Ph)Ph | CO | CH₂ | — | — |

TABLE III

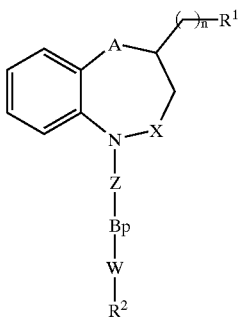

| No. | A | n | R¹ | R² | Z | X | Receptor Binding (% Inh. @ concentration in μM) V1a | V2 |
|---|---|---|---|---|---|---|---|---|
| 43 | S | 2 | OH | NHCO(2-CH₃,5-F)Ph | CO | CH₂ | 4% @ .1 | 0.028[1] |

[1] IC$_{50}$ values (μM)
[2] Enantiomers

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. The compound of formula I:

I wherein
R¹ is selected from —COOH, formyl, o-mesylate, —SO₂OH, alkoxysulfonyl, alkylcarboxy, substituted alkylcarboxy, aralcarboxy, substituted aralcarboxy, —NR⁴R⁵, —OH, cyano, N-morpholino, alkoxy, aralkoxy, alkylcarbamoyl, substituted alkylcarbamoyl, alkoxycarbonyl, —NHCOR⁶ and —CONR⁷R⁸, said substituted alkylcarboxy, substituted aralcarboxy, and substituted alkylcarbamoyl being independently substituted with one or more radicals selected from halogen, alkyl, alkoxy, and amino;

R⁴, R⁵, R⁶, R⁷, and R⁸ are independently selected from the group consisting of H, alkyl, and aryl;

A is S, SO or SO₂;

X is CH₂ or carbonyl;

Z is CH₂, SO₂ or carbonyl, with the proviso that X is not CH₂ when Z is CH₂;

B is (CH₂)$_m$, NH or O;

R² is —N(H)YR³ or —YN(H)R³ wherein Y is H or carbonyl:

R³ is H, alkyl, aryl or substituted aryl, said substituted aryl being substituted with one to three radicals independently selected from C₁–C₈ alkyl, C₁–C₈ alkoxy, fluorinated C₁–C₈ alkyl, fluorinated C₁–C₈ alkoxy, halogen, cyano, hydroxy, amino, nitro, C₁–C₄ alkylamino, C₁–C₄ dialkylamino, and unsubstituted, mono-, di- or tri-substituted phenyl; and W is aryl, substituted aryl, heteroaryl or substituted heteroaryl, wherein
said substituted aryl being substituted with one to three radicals independently selected from C₁–C₈ alkyl, C₁–C₈ alkoxy, fluorinated C₁–C₈ alkyl, fluorinated C₁–C₈ alkoxy, halogen, cyano, hydroxy, amino, nitro, C₁–C₄ alkylamino, C₁–C₄ dialkylamino, and unsubstituted, mono-, di- or tri-substituted phenyl, and
said substituted heteroaryl being substituted with one to three radicals independently selected from C₁–C₈ alkyl, halogen, aryl, heteroaryl, alkoxy, alkylamino, dialkylamino, arylamino, nitro, and hydroxy;

m is 1–3;
n is 1–5;
p is 0 or 1;

wherein each heteroaryl is independently a stable five- or six-membered monocyclic aromatic ring system which consists of carbon atoms and from one to three heteroatoms independently selected from N, O, or S; or an optical isomer, enantiomer, diastereomer, racemate or racemic mixture thereof, or a pharmaceutically acceptable salt thereof.

2. The compound of claim 1 wherein R¹ is selected from —COOH, formyl, o-mesylate, —SO₂OH, alkylcarboxy, substituted alkylcarboxy, aralcarboxy, substituted aralcarboxy, cyano, N-morpholino, alkoxy, aralkoxy, alkylcarbamoyl and substituted alkylcarbamoyl.

3. The compound of claim 2 wherein p is 0, A is S, and n is 1 or 2.

4. The compound of claim 2 wherein X is $CH_2$ and Z is carbonyl.

5. The compound of claim 2 wherein W is selected from phenyl, substituted phenyl, benzyl, substituted benzyl, pyridinyl, substituted pyridinyl, naphthyl and substituted naphthyl.

6. The compound of claim 2 wherein $R^2$ is —N(H)Y$R^3$ wherein Y is carbonyl and $R^3$ is substituted phenyl.

7. The compound of claim 6 wherein $R^2$ is —NHCO(2-Ph)Ph.

8. The compound of claim 2 wherein $R^3$ is phenyl or substituted phenyl.

9. The compound of claim 1 wherein $R^1$ is —N$R^4R^5$ —NHCO$R^6$ or —CONR$^7R^8$ wherein $R^4$, $R^5$, $R^6$, $R^7$ and $R^8$ are as claimed in claim 1.

10. The compound of claim 9 wherein
    $R^1$ is selected from —$NH_2$, —$NHCH_3$, —N($CH_3$)$_2$, —NHBOC, —N(BOC)$_2$, —NHCOC($CH_3$)$_2$$NH_2$, —N(COC($CH_3$)$_2$$NH_2$)$_2$ and —$NCH_2$ (2,5-OCH$_3$) Ph;
    W is Ph or substituted Ph;
    $R^2$ is —$NH_2$, —NHAc, —NHCO(2-CH$_3$)Ph or —NHCO(2-Ph)Ph; and
    p is 0.

11. The compound of claim 1 wherein $R^1$ is —OH.

12. The compound of claim 11 wherein
    W is heteroaryl, Ph or substituted Ph;
    $R^2$ is —$NH_2$, —NHAc, —NHCOCH$_3$, —NHCO(2-CH$_3$)Ph, —NHCO(2-Ph)Ph, —NHCO(2-CH$_3$,5-F)Ph, or —NHCO(3,4-Cl)Ph; and
    p is 0.

13. The compound of claim 1 wherein $R^1$ is alkoxycarbonyl, substituted alkoxycarbonyl or —CONR$^7R^8$ wherein $R^7$ and $R^8$ are as claimed in claim 1.

14. The compound of claim 13 wherein
    Z is carbonyl;
    W is Ph or substituted Ph;
    $R^2$ is —NHCO(2-Ph)Ph; and
    p is 0.

15. The compound of claim 1 which is 2-(2-carboxyethyl) 5-[4-(2-phenylbenzoylamino)benzoyl]-1,5-benzothiazepine.

16. The compound of claim 1 which is 2-carboxymethyl-1-oxo-5(4-(2-phenylbenzoylamino)benzoyl)-1,5-benzothiazepine.

17. The compound of claim 1 which is 2-carboxymethyl-5-(4-(2-phenylbenzolylamino)benzoyl)-1,5-benzothiazepine.

18. A substantially pure single enantiomer of the compound of claim 17.

19. A pharmaceutical composition comprising a compound according to claim 1 and a pharmaceutically acceptable carrier.

20. A method of treating a subject suffering from a condition of vascular resistance, which comprises administering to the subject a therapeutically effective amount of the compound of Formula I as defined in claim 1.

21. The method of claim 20 wherein said condition is selected from inner ear disorders, hypertension, congested heart failure, cardiac insufficiency, coronary vasospasm, cardiac ischemia, liver cirrhosis, renal vasospasm, renal failure, cerebral edema and ischemia, stroke, thrombosis, and water retention.

22. The method of claim 21 wherein said condition is congestive heart failure or cardiac insufficiency.

23. A process for preparing a compound of Formula Ia,

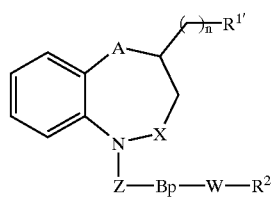

wherein $R^1$ is —COOH or formyl, alkoxy, aralkoxy, or —O(CO)$R^9$ wherein $R^9$ is alkyl, substituted alkyl, aryl or substituted aryl; said substituted alkylcarboxy, substituted aralcarboxy, and substituted alkylcarbamoyl being independently substituted with one or more radicals selected from halogen, alkyl, alkoxy, and amino;

A is S, SO or $SO_2$;

X is $CH_2$ or carbonyl;

Z is $CH_2$, $SO_2$ or carbonyl, with the proviso that X is not $CH_2$ when Z is $CH_2$;

B is $(CH_2)_m$, NH or O;

W is aryl, substituted aryl, heteroaryl or substituted heteroaryl; said substituted aryl being substituted with one to three radicals independently selected from $C_1$-$C_8$ alkyl, $C_1$-$C_8$ alkoxy, fluorinated $C_1$-$C_8$ alkyl, fluorinated $C_1$-$C_8$ alkoxy, halogen, cyano, hydroxy, amino, nitro, $C_1$-$C_4$ alkylamio, $C_1$-$C_4$ dialkylamino, and unsubstituted mono-, di- or tri-substituted phenyl;

$R^2$ is —N(H)Y$R^3$ or —YN(H)$R^3$ wherein Y is H or carbonyl;

$R^3$ is H, alkyl, substituted alkyl, aryl or substituted aryl; said substituted aryl being substituted with one to three radicals independently selected from $C_1$-$C_8$ alkyl, $C_1$-$C_8$ alkoxy, fluorinated $C_1$-$C_8$ alkyl, fluorinated $C_1$-$C_8$ alkoxy, halogen, cyano, hydroxy, amino, nitro, $C_1$-$C_4$ alkylamino, $C_1$-$C_4$ dialkylamino, and unsubstituted, mono-, di- or tri-substituted phenyl, and said substituted heteroaryl being substituted with one to three radicals independently selected from $C_1$-$C_8$ alkyl, halogen, aryl, heteroaryl, alkoxy, alkylamino, dialkylamino, arylamino, nitro, and hydroxy;

m is 1–3;

n is 1–5; and p is 0 or 1 wherein each heteroaryl is independently a stable five- or six-membered monocyclic aromatic ring system which consists of carbon atoms and from one to three heteroatoms independently selected from N, O, or S;

which processes comprises:

(a) reacting

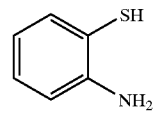

with a compound of Formula II to form a compound of Formula III.

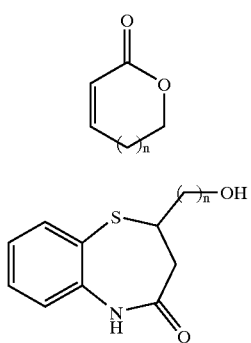

II

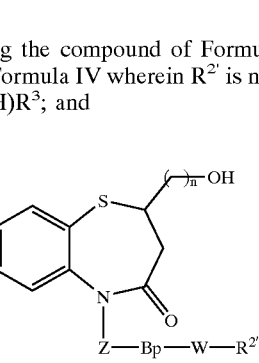

III (b) converting the compound of Formula III to a compound of Formula IV wherein $R^{2'}$ is nitro, —N(H)YR$^3$ or —YN(H)R$^3$; and

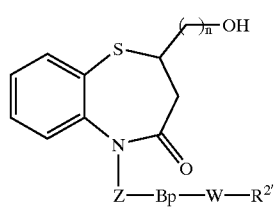

IV (c) converting the compound of Formula IV to the compound of Formula Ia.

24. A process for preparing a compound of Formula Ia

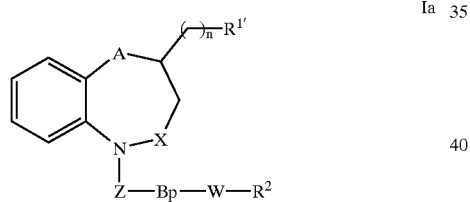

Ia wherein
R$^{1'}$ is —COOH or formyl, alkoxy, aralkoxy, or —O(CO)R$^9$ wherein R$^9$ is alkyl, substituted alkyl, aryl or substituted aryl; said substituted alkylcarboxy, substituted aralcarboxy, and substituted alkylcarbamoyl being independently substituted with one or more radicals selected from halogen, alkyl, alkoxy, and amino;

A is S, SO or SO$_2$;

X is CH$_2$ or carbonyl;

Z is CH$_2$, SO$_2$ or carbonyl, with the proviso that X is not CH$_2$ when Z is CH$_2$;

B is (CH$_2$)$_m$, NH or O;

W is aryl, substituted aryl, heteroaryl or substituted heteroaryl; said substituted aryl being substituted with one to three radicals independently selected from C$_1$–C$_8$ alkyl, C$_1$–C$_8$ alkoxy, fluorinated C$_1$–C$_8$ alkyl, fluorinated C$_1$–C$_8$ alkoxy, halogen, cyano, hydroxy, amino, nitro, C$_1$–C$_4$ alkylamio, C$_1$–C$_4$ dialkylamino, and unsubstituted mono-, di- or tri-substituted phenyl;

R$^2$ is —N(H)YR$^3$ or —YN(H)R$^3$ wherein Y is H or carbonyl;

R$^3$ is H, alkyl, substituted alkyl, aryl or substituted aryl; said substituted aryl being substituted with one to three radicals independently selected from C$_1$–C$_8$ alkyl, C$_1$–C$_8$ alkoxy, fluorinated C$_1$–C$_8$ alkyl, fluorinated C$_1$–C$_8$ alkoxy, halogen, cyano, hydroxy, amino, nitro, C$_1$–C$_4$ alkylamino, C$_1$–C$_4$ dialkylamino, and unsubstituted, mono-, di- or tri-substituted phenyl, and said substituted heteroaryl being substituted with one to three radicals independently selected from C$_1$–C$_8$ alkyl, halogen, aryl, heteroaryl, alkoxy, alkylamino, dialkylamino, arylamino, nitro, and hydroxy;

m is 1–3;

n is 1–5; and p is 0 or 1 wherein each heteroaryl is independently a stable five- or six-membered monocyclic aromatic ring system which consists of carbon atoms and from one to three heteroatoms independently selected from N, O, or S;

which process comprises:

(a) reacting

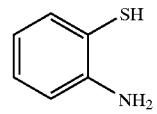

with a compound of Formula II to form a compound of Formula III.

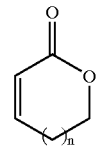

II

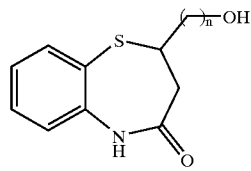

III (b) converting the compound of Formula III to a compound of Formula V;

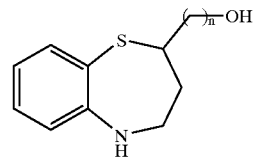

V (c) converting the compound of Formula V to the compound of Formula VI wherein $R^{2'}$ is nitro, —N(H)YR$^3$ or —YN(H)R$^3$; and

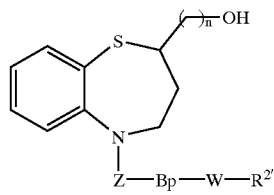
VI
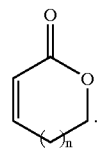
II
(d) converting the compound of Formula VI to the compound of Formula Ia.
25. A process for preparing a compound of Formula III
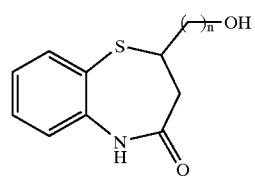
III
wherein n is 1–5,
which comprises reacting
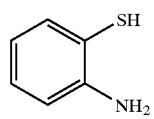
with a compound of Formula II
26. A compound of Formula III
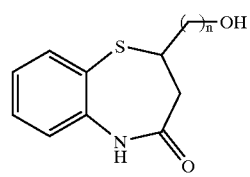
III
wherein n is 1–5.
27. The compound of claim 13 wherein $R^1$ is alkoxycarbonyl or —CONR$^7$R$^8$ wherein $R^7$ and $R^8$ are as claimed in claim 1.
* * * * *